(12) United States Patent
De Almeida Gusmao Lyra et al.

(10) Patent No.: US 12,714,553 B2
(45) Date of Patent: Aug. 25, 2026

(54) INTRAOCULAR LENS WITH FOCAL PERFORMANCE TAILORED TO PUPIL SIZE DEPLOYING REFRACTIVE POWER MODIFICATION ALONG SPIRAL TRACKS

(71) Applicant: Rayner Intraocular Lenses Limited, West Sussex (GB)

(72) Inventors: Joao Marcelo De Almeida Gusmao Lyra, Maceió (BR); Rodrigo De Abreu, Belo Horizonte (BR); Diogo Ferraz Costa, Belo Horizonte (BR)

(73) Assignee: Rayner Intraocular Lenses Limited, West Sussex (GB)

( * ) Notice: Subject to any disclaimer, the term of this patent is extended or adjusted under 35 U.S.C. 154(b) by 1086 days.

(21) Appl. No.: 17/779,779

(22) PCT Filed: Mar. 2, 2021

(86) PCT No.: PCT/BR2021/050091
§ 371 (c)(1),
(2) Date: May 25, 2022

(87) PCT Pub. No.: WO2022/183258
PCT Pub. Date: Sep. 9, 2022

(65) Prior Publication Data

US 2023/0338137 A1 Oct. 26, 2023

(51) Int. Cl.
*A61F 2/16* (2006.01)

(52) U.S. Cl.
CPC .......... *A61F 2/1618* (2013.01); *A61F 2/1645* (2015.04); *A61F 2002/1681* (2013.01)

(58) Field of Classification Search
CPC .................. A61F 2/16–1645; G01C 7/00–068
See application file for complete search history.

(56) References Cited

U.S. PATENT DOCUMENTS 5,408,281 A 4/1995 Zhang
5,507,806 A 4/1996 Blake
(Continued)

FOREIGN PATENT DOCUMENTS

AU 2019302757 A1 1/2021
BR 102016011774 A2 12/2017
(Continued)

OTHER PUBLICATIONS

Carl Rod Nave, Gullstrand's Equation, 2000 (Year: 2000).*
(Continued)

*Primary Examiner* — Thomas C Barrett
*Assistant Examiner* — Teresa M Dudden
(74) *Attorney, Agent, or Firm* — Harris Beach Murtha Cullina PLLC; Laura W. Smalley

(57) ABSTRACT

A new family of intraocular lenses that exhibit an extended depth of focus or a tailored multifocality where the lenses are designed by the combination of a base lens topology and additional refractive power range described along a spiral-like grid. The variety of parameters confer a great versatility to the lens design, which allows the achievement of the best suitable features to attend to a wide range of visual demands in performing different activities. It is possible to set the parameters to specify apt-focal lenses that account for optical performance changes due to pupil aperture variations, as well as to counter positive dysphotopic effects.

13 Claims, 13 Drawing Sheets

(56) References Cited

U.S. PATENT DOCUMENTS

| | | | | |
|---|---|---|---|---|
| 6,536,899 | B1 | 3/2003 | Fiala | |
| 8,647,383 | B2 | 2/2014 | Sanger et al. | |
| RE45,969 | E | 4/2016 | Hong et al. | |
| 9,690,882 | B2 | 6/2017 | Dobschal | |
| 9,703,018 | B2 | 7/2017 | Dobschal | |
| 9,918,831 | B2 | 3/2018 | Angelopoulos et al. | |
| 10,098,726 | B2 | 10/2018 | Gerlach et al. | |
| 10,278,809 | B2 | 5/2019 | Gerlach | |
| 10,386,654 | B2 | 8/2019 | Marshall et al. | |
| 2003/0117577 | A1 | 6/2003 | Jones et al. | |
| 2008/0269886 | A1 | 10/2008 | Simpson et al. | |
| 2009/0112314 | A1 | 4/2009 | Sarver et al. | |
| 2010/0161051 | A1 | 6/2010 | Hong | |
| 2011/0040377 | A1* | 2/2011 | Battis | G02C 7/022 623/6.32 |
| 2016/0074967 | A1* | 3/2016 | Sahler | B29D 11/023 425/162 |
| 2016/0157994 | A1* | 6/2016 | Gerlach | A61F 2/1627 623/6.27 |
| 2017/0196682 | A1 | 7/2017 | Lawu | |
| 2017/0245986 | A1 | 8/2017 | Canovas Vidal et al. | |
| 2019/0021847 | A1 | 1/2019 | Hong et al. | |
| 2021/0341757 | A1* | 11/2021 | Webber | G02C 7/06 |

FOREIGN PATENT DOCUMENTS

| | | | |
|---|---|---|---|
| CA | 2933459 | A1 | 12/2016 |
| DE | 102013215984 | A1 | 3/2015 |
| EP | 0622653 | A1 | 11/1994 |
| EP | 1468324 | B1 | 3/2006 |
| JP | H04181209 | A | 6/1992 |
| WO | WO-2010/009254 | A1 | 1/2010 |
| WO | WO-2011/099001 | A1 | 8/2011 |
| WO | WO-2012138426 | A2 | 10/2012 |
| WO | 2015022216 | A1 | 2/2015 |
| WO | WO-2020102514 | A1 | 5/2020 |
| WO | 2020260679 | A1 | 12/2020 |
| WO | WO-2021220007 | A1 | 11/2021 |

OTHER PUBLICATIONS

Diogo Ferraz Costa, Intraocular-Lens Design with Orthogonal Sinusoidal Pattern and Focal-Range Classification Algorithm, Belo Horizonte, 2020, pp. 1-63.

International Search Report and Written Opinion for Corresponding International Application No. PCT/BR2021/050091, Nov. 30, 2021, pp. 1-9.

Puell et al., "Disk Halo Size Measured in Individuals with Monofocal Versus Diffractive Multifocal Intraocular Lenses," J Cataract Refract Surg: 2015, 41:2417-2423 (7 pages).

Javitt, et al., "Cataract Extraction with Multifocal Intraocular Lens Implantation," Opthalmology 2000; 107: 2040-2048 (8 pages).

Ehmer, et al., "Einfluss verschiedener multifokaler Intraokularlinsenkonzepte auf den Streulichtparameter," Ophthalmologe 2011; 108: 952-956 (4 pages).

Alarcon, et al., "Preclinical Metrics to Predict Through-Focus Visual Acuity for Pseudophakic Patients," Biomedical Optics Express, May 1, 2016, vol. 7, No. 5; 1877-1888 (11 pages).

Extended European Search Report dated Jul. 14, 2023 for the corresponding European Patent Application No. EP 21923626.2 (13 pages).

* cited by examiner

INTRAOCULAR LENS WITH FOCAL PERFORMANCE TAILORED TO PUPIL SIZE DEPLOYING REFRACTIVE POWER MODIFICATION ALONG SPIRAL TRACKS

CROSS REFERENCE TO RELATED APPLICATION

This Application is a 371 of PCT/BR2021/050091 filed on Mar. 2, 2021, the content of which is incorporated herein by reference.

FIELD OF INVENTION

The present invention relates to an ophthalmic intraocular lens, phakic or pseudophakic, meant to have its focal performance tailored to different pupil sizes, ensuring acceptable contrast of the retinal image and visual preferences and needs of the patient. The lens deploys refractive power variation, microlenses, or both, along spiral tracks to achieve this goal.

BACKGROUND OF THE INVENTION

An intraocular lens is used in addition to or to replace the natural lens of the eye (crystalline lens), mostly when the latter is affected by cataract. In cataract surgery, the crystalline lens is removed, often preserving the capsular bag where the intraocular lens is inserted. This artificial lens can be developed to provide a good visual acuity for a single object distance, called monofocal lens, or for several object distances, thus referred to as multifocal.

The simplest monofocal lens is the one with spherical surfaces. In these lenses the amount of spherical aberration becomes increasingly more detrimental to the image contrast in a distant focal point as the pupil is dilated. This issue can be mitigated by deploying at least one aspheric surface to the lens, which imparts a smooth reduction of the curvature radius from the center to the border, therefore reducing the contribution of spherical aberration. This aspheric surface can also be designed to compensate for some or all the spherical aberration present in the cornea. Both spherical and aspheric monofocal lenses provide a single focal distance, generally to favor far vision. Objects closer to the eye then have its optimal image projected on a plane off the retina.

The focal spot, Point-Spread Function (PSF), of a point object distant from the eye features a minimum spot dimension at the exact focal plane of the system for distant vision. This plane is often the retina. The spot size is larger on longitudinally adjacent planes along the optical axis. However, there is a maximum spot size deviation from that of the optimal focal spot that is still perceived as yielding good resolution. The distance of the plane, on which this acceptable enlarged spot is projected, to the focal plane, is referred to as depth of focus.

Spherical lenses, despite the worse quality of the focal spot on the focal plane, are known to feature larger depths of focus than their aspheric counterparts. The latter, on the other hand, offer better and smaller focal spots, thus higher contrast, and therefore better resolution.

The pupil size naturally changes for different illumination conditions and, for both spherical and aspheric lenses, the depth of focus and contrast change as the pupil diameter varies. Since intraocular lenses do not usually feature the accommodation mechanism present in the crystalline lens, which partly compensates the pupil size variations, their contrast and depth of focus are often not in tune with the functional needs of the patients throughout the full range of pupil diameters. A person with an implanted aspheric monofocal lens might benefit from high-contrast and reasonable field range for distant vision under photopic light conditions (bright scene), but this individual still suffers from a poorer vision and limited field range under mesopic and scotopic conditions (medium lit to dark scenes). The same patient would have poor contrast for objects ranging from intermediate to close distances, regardless the pupil size.

Unlike monofocal lenses, which are designed for good visual acuity for distant objects, the multifocal lenses are designed for a good visual acuity for objects at different distances. Objects at different distances yield their images overlapped on the retina in a process called simultaneous vision. This intraocular rivalry is partly sorted out by neural processes, such as neural adaptation or neural resignation, which allows the patient to privilege the image of the object of interest at any particular moment.

Multifocal lenses usually have the optical zone partitioned into specific areas, resulting in different optical powers to yield more than one focal plane. A bifocal lens often creates a focal plane for far vision and another for near vision, while a trifocal lens has one more focal plane, often for intermediate vision. In most cases, multifocal lenses have a refractive central area with the reference optical power and at least one other area with an additional positive optical power which can be refractive, diffractive or a combination of both. The diffractive pattern in the periphery delays and bends the light propagation in such a way that the constructive and destructive interference orders are used to create a focal point other than the central one. In these lenses there tends to be intermediate distances along which the visual acuity is far lower than that on the designed target distances or foci.

Multifocal lenses, in addition to the contrast reduction of the main focus, can have some positive dysphotopsia drawbacks such as halos, rings and glare. Glare is due to diffraction effects and halos are perceived as the background defocused images due to other foci. Although particularly glare can be bothersome when reading from a shiny page or driving towards the sun, these effects are especially adverse in darker environments (M. C. Puell, M. J. Pérez-Carrasco, F. J. Hurtado-Ceña, L. Álvarez-Rementeria, "Disk halo size measured in individuals with monofocal versus diffractive multifocal intraocular lenses," Journal of Cataract & Refractive Surgery, 2015. Jonathan C Javitt, Roger F Steinert; "Cataract extraction with multifocal intraocular lens implantation: A multinational clinical trial evaluating clinical, functional, and quality-of-life outcomes", Ophthalmology, 2000). Diffractive and segmented multifocal intraocular lenses with sharp transitions yield more perceived stray light than refractive multifocal designs (A. Ehmer, T. M. Rabsilber, A. Mannsfeld. M. J. Sanchez, M. P. Holzer, G. U. Auffarth, "Einfluss verschiedener multifokaler Intraokularlinsenkonzepte auf den Streulichtparameter," Der Ophthalmology, v. 10, 2011).

Extended-depth-of-focus (EDoF) lenses, also called wide-depth-of-focus lenses, or lenses for extended range of vision, are sometimes included in the category of multifocal lenses, but should be more appropriately classified in their own category. They can be designed so that the depths of focus around different focal planes partly overlap, or such that the depth of focus about a single focal plane is wider, guaranteeing a visual acuity above a certain widely acceptable threshold value throughout its envisioned range. The higher, more constant and smoother the visual acuity is throughout the extended range, the more comfortable it is for vision within those distances, restoring part of the accommodation loss due to the crystalline removal. International standards, as the ANSI Z80.35-2018, prescribe certain attributes to be met in order for a lens to qualify as EDoF. Pseudophakic patients implanted with EDoF lenses that deliver good visual acuity from long to short distances are expected to experience reduced spectacle dependency. The same applies to phakic patients with an advanced state of presbyopia.

The visual acuity of the optical system as an eye can be measured by means of the MTF—Modulation Transfer Function (Alarcon, Aixa & Canovas, Carmen & Rosen, Robert & Weeber, Henk & Tsai, Linda & Hileman, Kendra & Piers, Patricia. "Preclinical metrics to predict through-focus visual acuity for pseudophakic patients". Biomedical Optics Express, 2016). The MTF represents how good the contrast is for a given spatial frequency by representing the amplitude with which different line-pair frequencies are formed on the image plane. It can be obtained by applying a spatial Fourier Transform to the PSF that describes how the energy irradiated by an object point and entering the eye is distributed on the image plane. Therefore, the PSF at the retina is also known as the impulse response of the eye optical system. Therefore, every infinitesimal point in an object to be imaged is represented by a finite intensity distribution (spot) on the image plane, whose pattern depends both on diffractive and refractive phenomena. The image of any object is then represented as a convolution of each point of the object and the PSF corresponding to this point in the image plane (retina).

What has still been lacking in the prior art is an intraocular lens design that can be optimally tailored to the focal and contrast performance that best attends to the needs of certain user classes according to their functional profile, considering object proximity and size, illumination level, pupil size and desired focal range, simultaneously reducing positive dysphotopic effects and sensitivity to decentration upon implantation.

Examples of activities composing a typical functional profile of a given class of patients are driving at night, reading from an illuminated smartphone screen, reading labels, shaving, applying makeup, working on a computer, cooking, interacting with other people in a room, walking up and down stairs and watching TV.

Night driving requires the clear view of traffic, signs and features on the car dashboard while the pupil is large due to low illumination levels of the scene. This calls for an acceptable contrast at reasonable spatial frequencies for distances ranging from far to intermediate vision (>6 m to 0.5 m), and reduced positive dysphotopsia, such as halos and glare.

Reading from a close screen, reading labels, shaving, applying makeup, working on a computer, cooking and watching TV, on the other hand, require high contrast at considerably higher spatial frequencies and smaller pupils, due to a better lit scene, for a distance range from far intermediate (2 to 4 m) to very close (0.35 to 0.5 m).

Comfortable visual interaction with other people in a room and walking up and down stairs pose moderate demands on contrast at medium spatial frequencies from short to far intermediate distances (0.35 to 4 m) across a wide range of illumination conditions, therefore, across a wide range of pupil sizes (2-6 mm).

Therefore, the present invention comprises a new design philosophy using power variation distributions through the deployment of microlenses, periodic variations and helical steps in spiral grids defined over a modified base lens surface, with the intent of providing custom optical performance suited for the needs of the patient. These needs may include a general activity profile that helps in determining the optimal design parameters. The parameters can be defined to compensate for scenes with different levels of illumination and the associated pupil size variations; object distance and size variations; as well as to partly or completely mitigate positive dysphotopic phenomena, such as halo and glare.

DESCRIPTION OF THE PRIOR ART

A number of patents describe ophthalmic lenses with optical power modifications on the lens surface for various reasons and using different methodologies, including multifocality and extended depth of focus. Some of them propose spiral distributions and others the deployment of microlenses, as is discussed below.

U.S. Pat. No. 8,647,383 B2 proposes an intraocular lens with at least one region with refractive power greater than the base dioptric power and one region with refractive power lower than the base dioptric power. It also uses a polynomial approach to the lens power calculation with radial symmetry and azimuthal independence. The design claims robustness to decentration, however it is dependent on the periodicity of the refractive power pattern, which depends on the pupil size.

U.S. Pat. No. RE45969 E presents an intraocular lens that has a transition region in a concentric annular zone composed of a stepped surface elevation variation. This transition region can be linear or nonlinear, and there can be any number of step variations. This invention proposes an extended range of vision but offers limited flexibility to meet smooth and tailored focal performance across different pupil sizes. Besides, this proposed design is more prone to decentration effects.

US patent no. 20100161051 A1 specifies an intraocular lens with a modulated sinusoidal profile as a function of the radius on the surface of the lens, ranging from the center to the edge. The sinusoidal function can be modulated in amplitude or frequency and is distributed in concentric annular regions only. There is no sinusoidal variation along the azimuthal coordinate and there is little flexibility to guarantee smooth and tailored focal performance across different pupil sizes.

Some lenses are based on a non-rotationally symmetrical design, as using, for example, additional optical power variation distributed along a spiral track.

Patent EP 1468324 B1 by Johnson & Johnson Vision Care includes multifocal ophthalmic lenses with refractive surfaces containing spiral patterns. It contemplates a smooth transition between spiral regions and implements a logarithmic spiral.

Patent EP 0622653 A1 specifies a bifocal contact lens where the transmittance, color filter, diffraction grating, or undulating profile is changed in a step-like manner, generating a continuously varying power profile. The reason for the adoption of the spiral tracks was solely to enable better circulation of the tear film between the cornea and the contact lens.

U.S. patent Ser. No. 10/579,95338 B2 describes an entirely refractive spiral or helicoidal structure for an ophthalmic lens. This structure is restricted between 0 and $2\pi$ radians with increasing elevation, yielding a power change and wide depth of focus that remains the same for different pupil sizes. The discontinuity between the starting and ending region of the spiral structure can be smoothed using a Gaussian profile. The design is based on a single spiral track and restricted to one turn, which always requires the need for a rather large or abrupt transition region connecting the start and the end of the spiral track. The alignment of this region is prone to compromise the contrast in the respective meridian, therefore lens rotation upon implantation might change the user experience.

Patent JPH 04181209A presents a contact lens that possesses a spiral pattern in which the additional refractive power comes from varying the refraction index across the pattern.

U.S. Pat. No. 9,690,882 B2 introduces an intraocular lens intended as an extended-depth-of-focus lens in which the total refractive power is the sum of a base lens power with a structural power profile. The patent targets a thin intraocular lens having a structural topological component based on a Fresnel profile, a Diffractive Optical Element (DOE) or on a variation of the refractive index, in a grating fashion, modulated by a single spiral track with increasing azimuthal power involving a single helical turn. The helical base on either the anterior or posterior surface is meant to add varying power to the power on the opposite surface. The incorporation of either a Fresnel or a grating pattern superimposed on a helical base on one of the lens surfaces is meant to split the base power between the anterior and posterior surface resulting in a thinner lens. The Fresnel and DOE grating structural profiles, however, are both diffractive and susceptible to a larger degree of positive dysphotopsia. Additionally, the modulation of the refractive index is to date a method with limited spatial precision deficient controlled batch fabrication possibilities in industrial processes. Also, the fact that the spiral is defined between 0 and $2\pi$ radians, in a single helical turn, creates a discontinuity in the profile. That can be softened by a transition region connecting the beginning of the spiral track to its end. Nevertheless, such a design is prone to offer vision artifacts across the meridian where the discontinuity or the transition region occurs, compromising vision acuity and altering the visual experience of the user depending on lens rotation upon implantation. This design could require a marking to assist implantation, avoiding angles coincident with frequent patterns in scenes. Besides, the fact that the spiral track has only one turn limits its design capability and makes it less susceptible to decentration effects relative to the pupil center.

Patent US20090112314A1 uses microlenses disposed of in a grid, or randomly distributed, to locally add optical power to that of the base intraocular lens creating a spherically asymmetrical distribution of the light. The microlenses are used to focus the light on the optical axis providing an additional optical power to the base lens power to achieve multifocality. Its core claim is to provide multifocality with reduced perception of stray light artifacts, such as glare and halo, compared to other multifocal intraocular lens designs, by deploying asymmetrical distribution of the microlenses over the optical area. The efficacy of this strategy can be dependent on the adequate implantation in both eyes and requires that the asymmetrical microlens pattern of one lens in relation to the other is reflected up and down, or right and left. Patent WO2019/166654A1 uses a similar structure where the main difference from patent US20090112314A1 is that the microlenses are used to focus the light out of the optical axis, in the periphery of the foveola, in an attempt to halt the rate of myopia increase.

Patent CA2933459A1 proposes a contact lens that deploys positive microlenses added to the base lens to generate a small blur along the retinal surface without compromising image quality at the fovea, in a claim to reduce or slow down the progression of myopia.

U.S. Pat. No. 5,507,806A presents an intraocular lens with microlenses designed to create images of the object in different areas of the retina in patients with AMD (Age-related Macular Degeneration).

Patent US20110040377A1 presents a multifocal intraocular lens with a flat base containing microlenses of different optical powers distributed along circular patterns, grids or even randomly.

Patent BR102016011774A2 defines an intraocular base lens that consists in two separate parts to be fused with microlenses disposed inside the lens. It proposes to achieve an extended depth of focus.

Spectacles and sunglasses with microlenses on the lens surface were presented in U.S. Ser. No. 10/386,654. The different additional refractive powers of the microlenses were used to achieve multifocality while keeping the glass thickness relatively thin.

Patent WO2012138426A2 uses the effect of multiple pinholes with or without a microlens attached to each pinhole spot to reach a depth of focus of up to 3 diopters. The existence of pinholes intrinsically indicates that there are opaque regions on the lens surface, reducing the total amount of light allowed into the eye, therefore leading to the compromise of a reduced contrast.

Even though these patents address different solutions to individual issues, each one of them has some sort of limitation or a purpose different than that proposed in the current invention, as aforementioned. The lens design proposed in this invention is unique in the sense that it allows the focal range to be tailored for various object distances, taking into account scenes under different illumination levels. This can be achieved by modelling the additional refractive power distributed over a spiral-like grid, that can either lead both to a certain robustness to pupillary variations or to a custom behavior for different pupil apertures.

SUMMARY OF THE INVENTION

The present invention relates to an ophthalmic intraocular lens, phakic or pseudophakic, meant to have its focal and contrast performance tailored to different pupil sizes, ensuring acceptable contrast of the retinal image and compliance to the visual needs of certain patient classes according to their respective functional profiles. In general, this is an apt-focal lens that can be designed to be best suitable to a given range of visual demands. These requirements can be accomplished by means of additional power variations inserted along spiral tracks and microlenses applied over a modified base aspheric lens.

In one particular embodiment the lens is designed to achieve a smooth and approximately constant good visual acuity from distant through near vision for different pupil sizes. This lens has power distributions that modify the base lens power profile along two Archimedean spiral tracks, that extend from the edge of a central circular region to the lens periphery or to some point within the optical zone. In this embodiment (shown in FIG. 4), the anterior and posterior surfaces have pre-defined base functions, with the front surface featuring the additional deviations to the power distribution by functions described within spiral tracks 24. The back surface 40 does not have power deviations from the base profile. Between the front and back surfaces, a cylindrical region, whose thickness can range from 0 to 3 mm, is added 30. The two contiguous Archimedean spiral tracks 24 have equal widths and each of them comprises 2.5 cycles. The additional power profile along the spiral tracks can be limited by a circular area 28 smaller or equal to the lens radius, as indicated in FIG. 2. The same surface also has another circular central area 22, smaller than 28, from which the spiral pattern evolves from the center to the periphery of the surface.

Another embodiment of the lens, FIG. 5, shows a contiguous biconvex lens where the spiral extends from the anterior aspheric reference surface to the posterior reference aspheric surface, without any intermediate part connecting both surfaces. In this embodiment there are four Archimedean spiral tracks 24 starting at the edge of the central circle 22 of the front surface 20 and extending to the edge of a central circle on the back surface 40.

The power distribution in any of the aforementioned embodiments can be described by either discrete or periodic functions, as microlenses dotting the spiral track (FIG. 8) or a sinusoidal function along the track (FIG. 10), or both. The power-distribution topology can be employed on either the anterior surface, or the posterior surface, or both surfaces, or even inside the lens. The power distribution along spiral tracks is intended to gradually insert the necessary additional power to keep the acceptable visual acuity as desired over a range of focal planes as the pupil aperture varies. The additional power can be positive or negative in relation to the reference refractive power of the base lens. Therefore, the actual refractive power of the lens results from the combination of the reference power and the added power.

The reference refractive power of the lens, responsible for the correction of defocus in myopic and hyperopic eyes, depends on the spherical equivalent curvatures of the anterior and posterior surfaces, on the lens central thickness and on its refractive index.

In a particular embodiment, the underlying base surface is designed with annular aspheric segments, as in FIG. 11, whose asphericities change linearly, or following other functions, described by a Taylor series, a Fourier series, Bessel functions, Jacobi polynomials or Lagrange polynomials. This function determines the shape of the transition region, between the values of conic constants, defined at the inner and outer radial edges of each segment (FIG. 12). This architecture enables the optimization of parameters to enhance image contrast at different pupil sizes and to partly counterbalance the reduction of the depth of focus that accompanies pupil dilation.

FIG. 6 presents the profile of another particular embodiment, where two spiral tracks define regions of the base lens surface to be shifted downwards parallel to the optical axis of the lens 14, in a helical fashion. To avoid abrupt steps (h1*a* through h1*d* and h2*a* through h2*d*) between spiral tracks in adjacent turns, a surface transition is imparted by a continuous function. This transition uses a percentage of the radial dimension of the spiral tracks and is designed to confer a different optical power to the lens, other than that of the base surface. The transition zone can occupy from 0% to 100% of the spiral track width, with 0% meaning an abrupt transition while 100% yields the smoothest transition. The transition function can follow a linear function, or a continuous function described by a Taylor series, a Fourier Series, Bessel functions, Jacobi polynomials or Lagrange polynomials, but it is preferably defined by a smooth truncated sinusoidal function. The transition function has different amplitudes along the azimuthal position due to the spiral nature of the steps. This transition function can also be different for distinct spiral tracks. This embodiment based on steps could have any number of spiral tracks between 1 and 200 and different types of spirals. The base lens surface topology can be described by different functions as aspheric, spherical, toric or multi-aspheric, for example. The zones defined by the spiral grid can also have additional power distributions along them, such as microlenses or other types of functions. In this embodiment, each transition from one spiral track to another can have equal step heights (as h1*a* through h1*d* or h2*a* through h2*d* in FIG. 6) or the height can vary with the azimuthal angle. In this particular embodiment, the posterior surface is a simple aspheric.

FIG. 7A shows a possible three-dimensional representation of this structure, where the transition regions 52 and 54 occupy different radial extensions of their respective spiral tracks 12*b* and 12*a*.

The transitions between the base surface profile and that of the additional power distribution along the spiral track are preferably smooth, avoiding adverse effects as local stray-light artifacts resulting, for instance, from sharp angles between the base of individual microlenses and the surrounding topology.

The surfaces of all aforementioned embodiments can be conferred a toric shape to account for astigmatism. The anterior base surface, or the posterior base surface, or both base surfaces can be designed as simple aspheric, spherical, toric or as modified aspheric surfaces.

By deploying variations of refractive power, microlenses, or both along spiral tracks, this invention offers the versatile possibility to tweak multiple design parameters to tailor an intraocular lens exhibiting a focal performance that best suits the needs of certain user classes according to their functional profile. The lens design can consider the object proximity and size, illumination level, pupil size and desired focal range, simultaneously reducing positive dysphotopic effects and sensitivity to decentration upon implantation.

One skilled in the art should understand that the plurality of parameters available in the current invention enables the design of a lens that conforms to the strict performance demands imposed by international standards and user functional profile needs, considering focal and contrast performance at different distances, illumination conditions and pupil sizes. The resulting lenses are then more than mere multifocal or EDoF lenses; they are actually signature lenses with tailored performance spanning a range of circumstances unparalleled by any other.

DESCRIPTION OF THE ELEMENTS OF THE INVENTION

The elements of this invention are taught using an intraocular lens whose diameter is in the range from 4 to 10 mm. Preferably, the lens diameter is considered 6 mm, whose diameter value is used to define the ranges of the parameters of the invention. The reference refractive optical power of the lens, given by the Eq. 1, ranges from 5 D to 30 D.

$$\Phi_{IOL} = \frac{(n_{IOL}-n_{aq})}{R_{ant}} + \frac{(n_{vit}-n_{IOL})}{R_{pos}} - \left[\frac{(n_{IOL}-n_{aq})}{R_{ant}} \cdot \frac{(n_{vit}-n_{IOL})}{R_{pos}} \cdot \frac{t_{IOL}}{n_{IOL}}\right] \quad \text{Eq. 1}$$

Where $\Phi_{IOL}$ is the base refractive power, $R_{ant}$ is the radius of curvature of the anterior surface, $R_{pos}$ is the radius of curvature of the posterior surface, $t_{IOL}$ is the lens center thickness and $n_{IOL}$, $n_{aq}$ and $n_{vit}$ are the refraction indices of the intraocular lens, aqueous humor and vitreous humor, respectively.

The power profile over the lens surface is obtained by the combined topographical variations over the lens surface of all the elements included in a given embodiment, as a power-distribution function following the spiral tracks, the microlenses along those tracks and the base surface.

Figure 2:
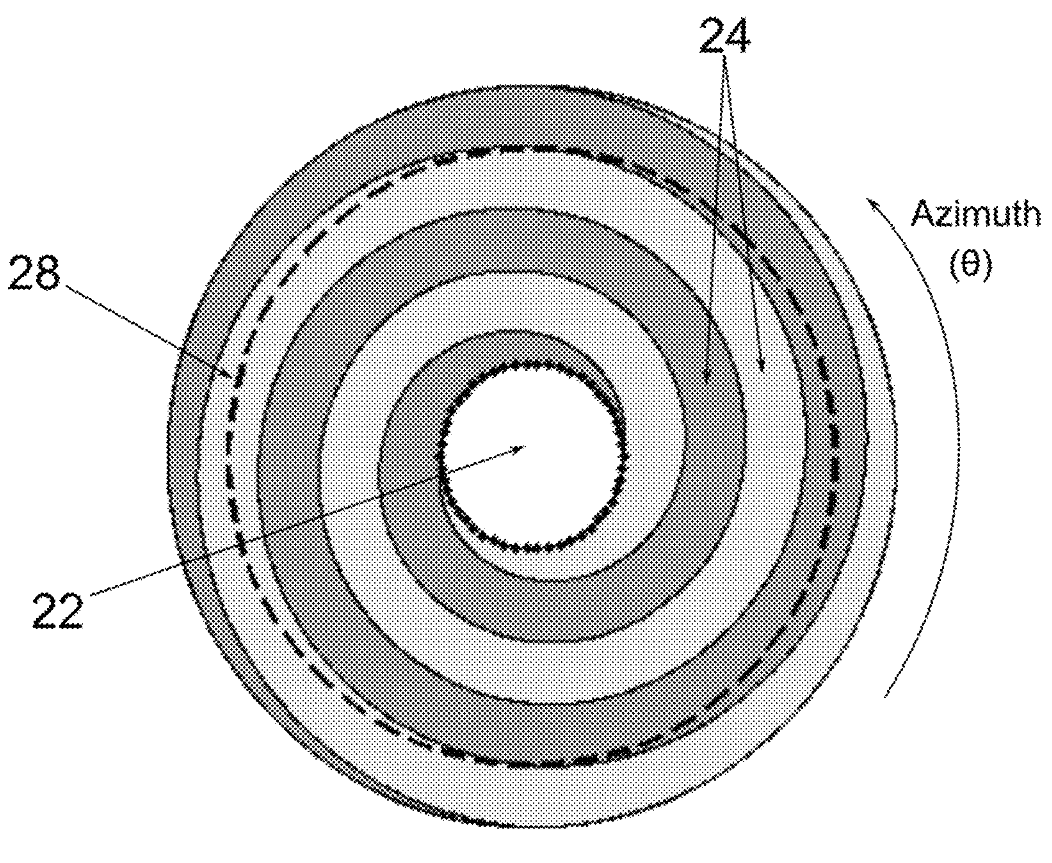
FIG. 2—Example of a base lens surface, containing a grid defined by two Archimedean spiral tracks 24, a circular central zone 22, and an outer circular region 28 that limits the range of the power variation along the spiral tracks.
Figure 13:
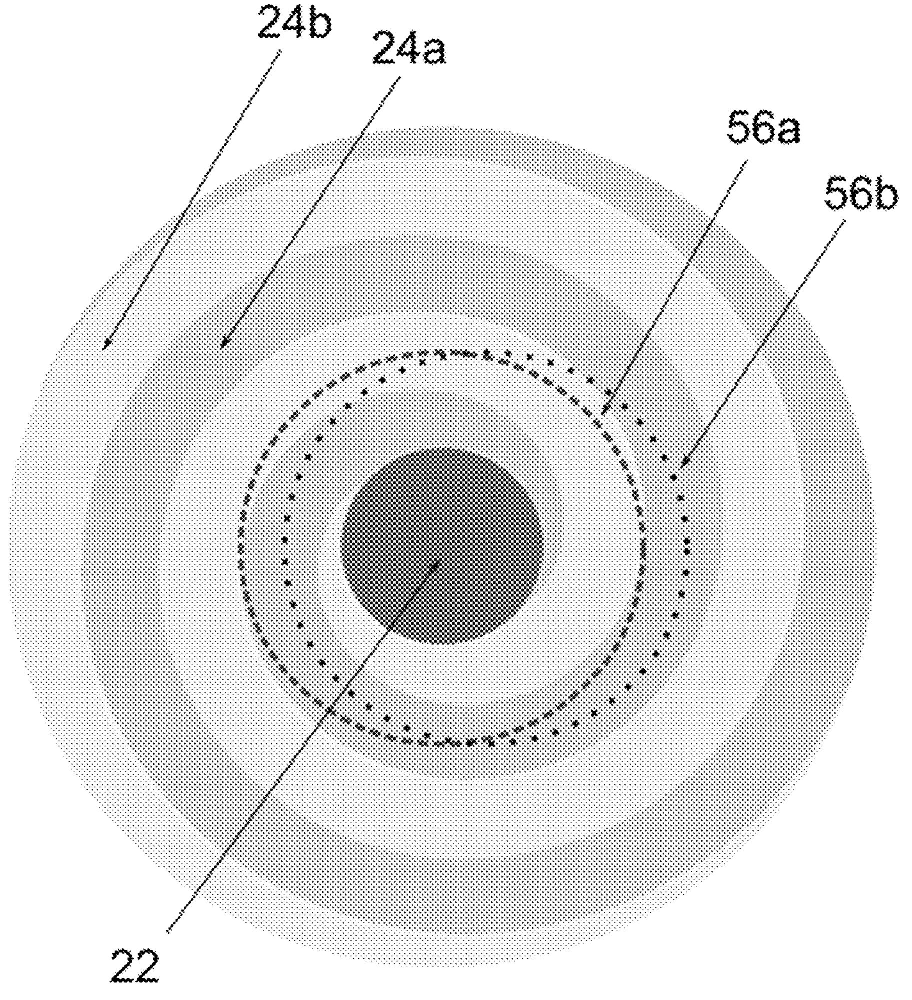
FIG. 13—Example of a centered 56*a* and a decentered 56*b* situation of a lens with a spiral grid with respect to the pupil aperture.

Spiral tracks vary both with the radius from the center to the edge of the lens and with the azimuthal angle, as shown in FIG. 2. They guarantee a smooth transition of features as the pupil size changes. As no complete turn of a spiral track is ever inscribed in a concentric circle, a lens with optical features on a spiral track can be designed to be less prone to deleterious decentration effects than one with concentric zones, also less dependent on the pupil variation. FIG. 13 illustrates an example of a lens surface with two Archimedean spiral tracks 24*a* and 24*b*. Consider, for example, that each spiral track has its own additional focal power, with spiral track 24*a* giving the intermediate focal power and spiral track 24*b* the near focal power, and that the lens and the pupil 56*a* are centered on the optical axis. If a decentration on the lens position in the eye occurs, making the pupil area over the lens surface to change from pupil 56*a* to pupil 56*b*, the amount of intermediate and near focal power does not change significantly. The smaller the width of the spiral tracks 24, the greater the robustness of the lens to decentration effects. Changes in refractive power along the spiral tracks enable contrast and depth of focus to be maintained, prioritized, or mutually mediated, as the pupil gradually changes.

A suitable modulation of the additional power along spiral tracks can also reduce the onset of positive dysphotopic effects on the retina, generally perceived as radially symmetric and concentric circular patterns due to the likewise concentric regions on the lens design. The mitigation of this adverse effect is particularly important when viewing far objects in a scotopic condition, in which the pupil is dilated.

Figure 1:
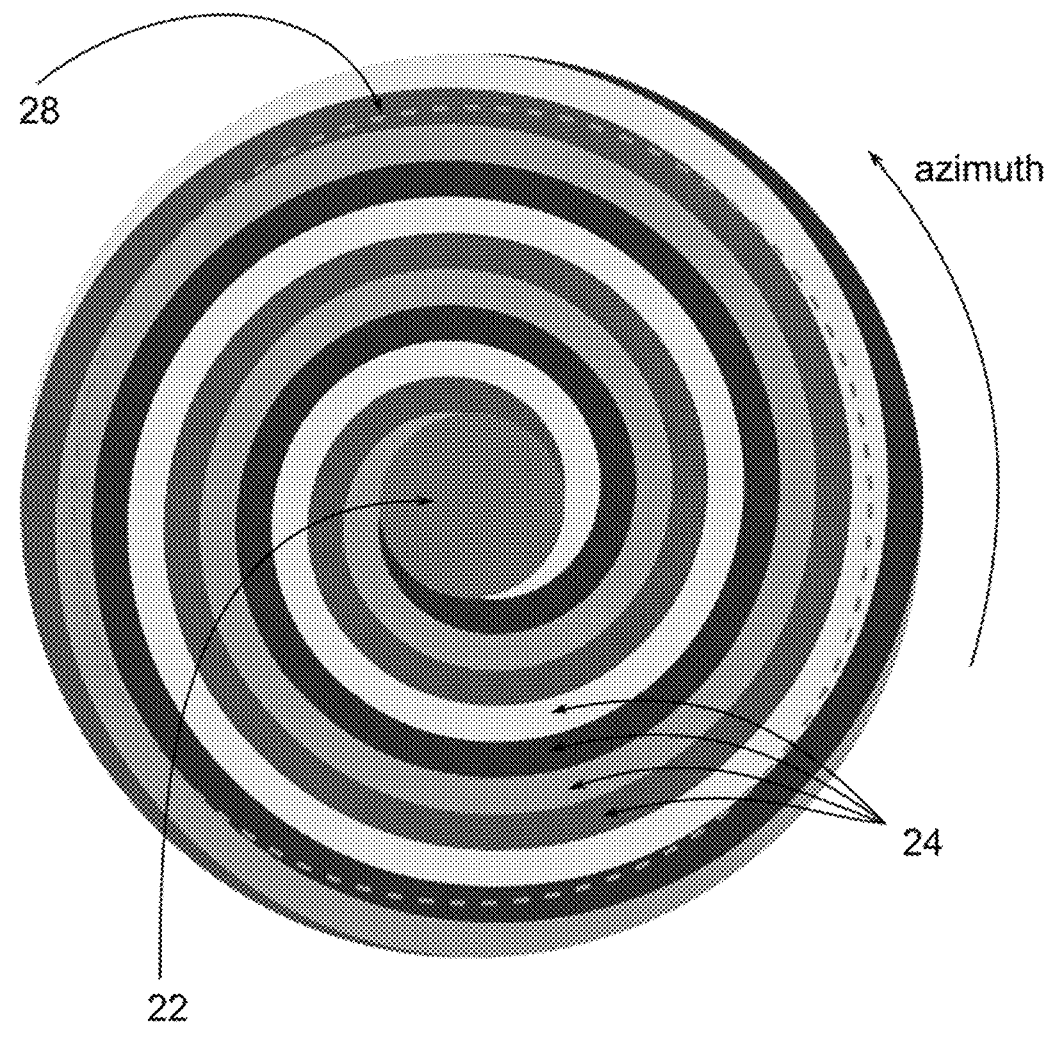
FIG. 1—Example of a base lens surface, containing a grid defined by four Archimedean spiral tracks 24, a circular central zone 22 from which the spiral grid pattern evolves outwards, and an outer circular region 28 that limits the range of the power variation along the spiral tracks.
Figure 3:
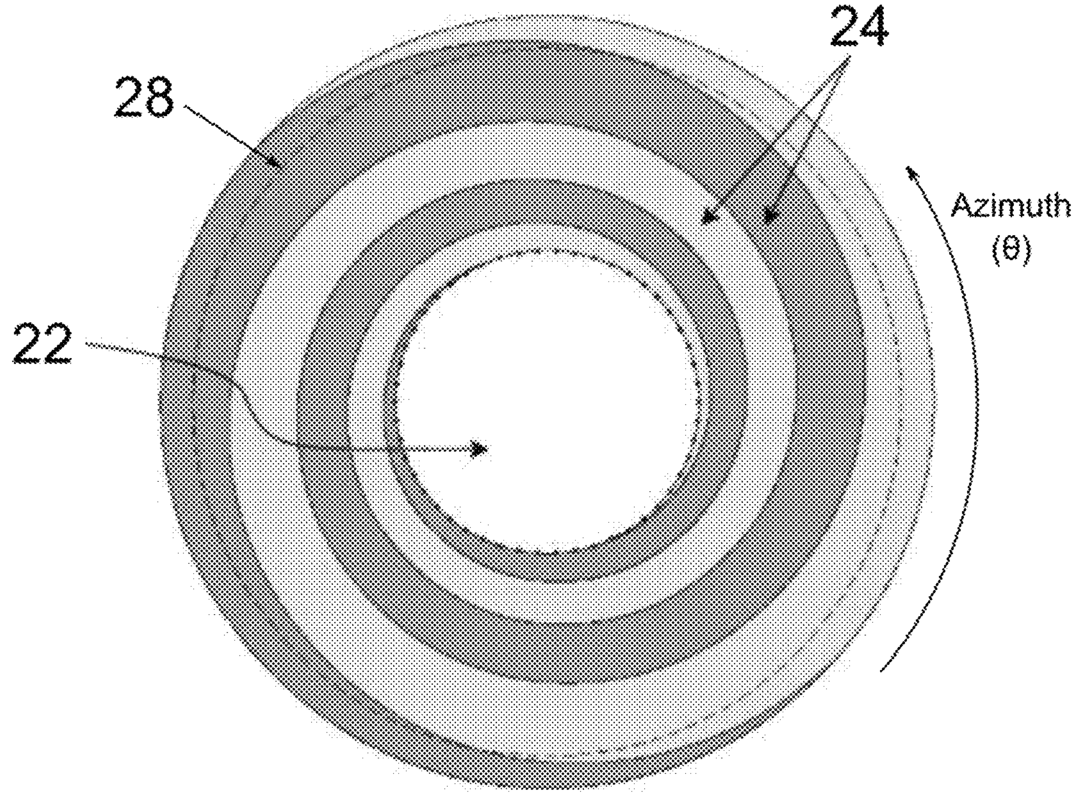
FIG. 3—Example of a base lens surface, containing a grid defined by two logarithmic spiral tracks 24, in which the width of each track increases with the azimuthal angle.
Figure 4:
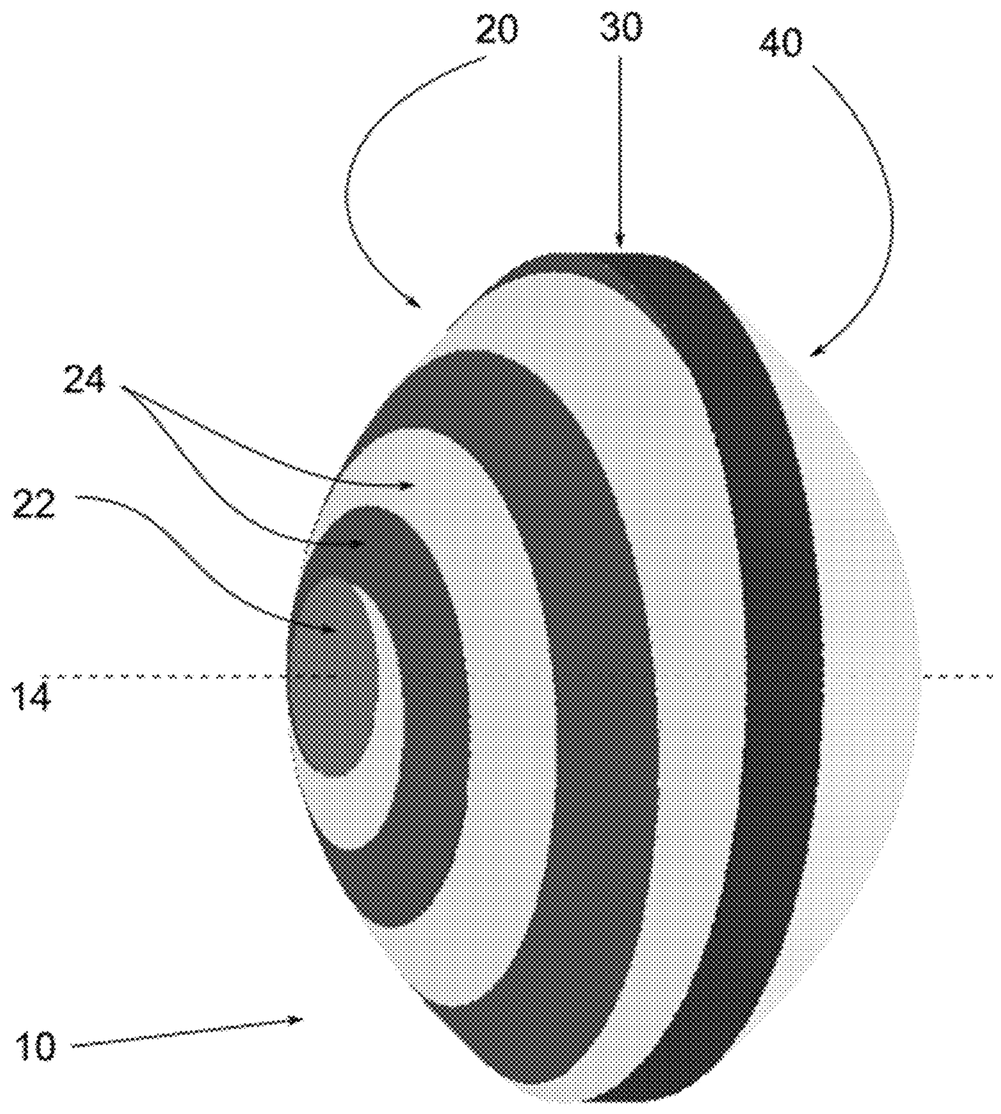
FIG. 4—Lateral view of one lens 10 embodiment, where its anterior surface 20 contains a grid defined by two Archimedean spiral tracks 24, and its posterior lens surface 40 follows an aspheric topology. Also, a cylindrical body 30 is inserted between the anterior 20 and posterior 40 surfaces.
Figure 5:
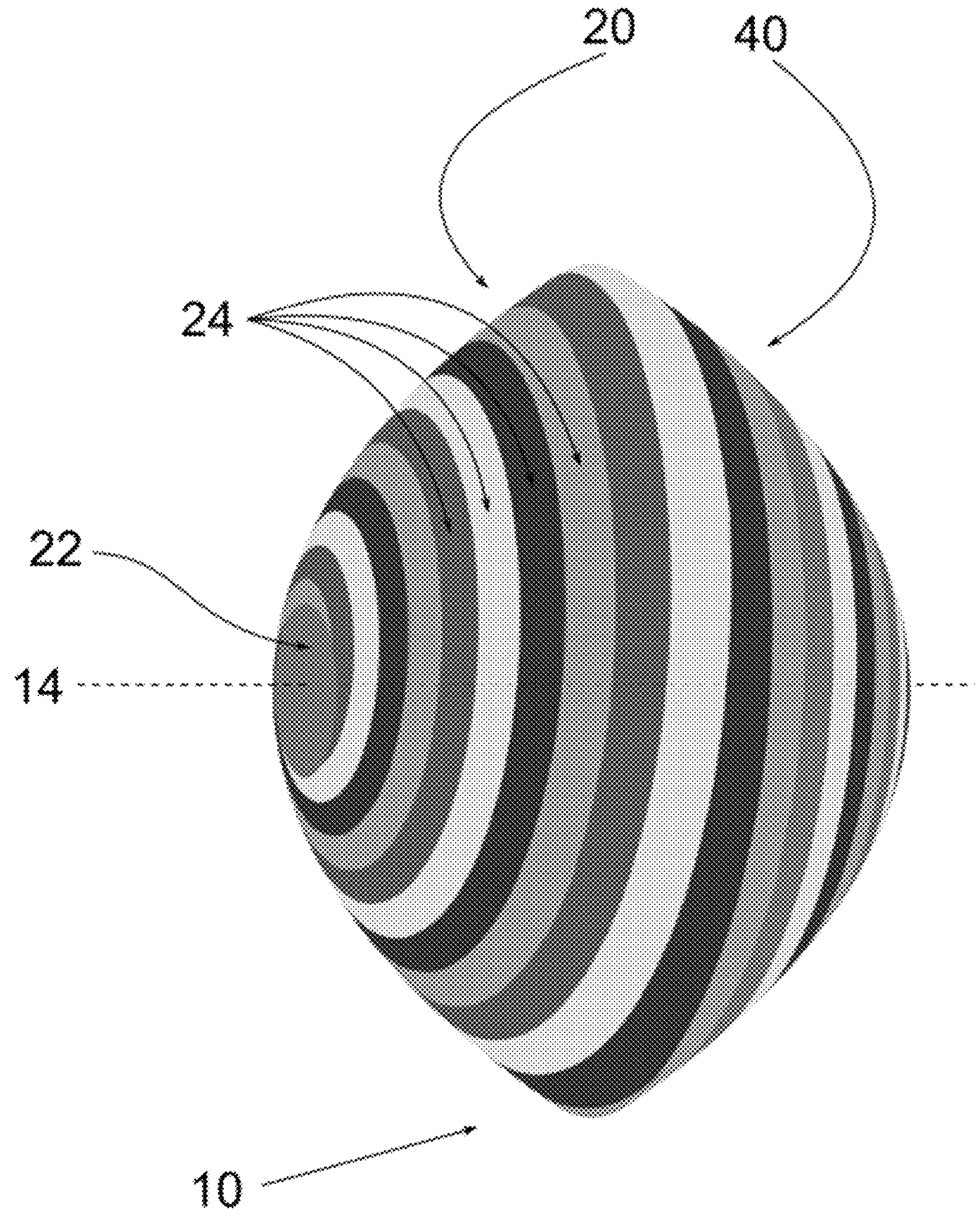
FIG. 5—Lateral view of one lens embodiment that contains a grid defined by four Archimedean spiral tracks 24 seamlessly extending from the anterior surface 20 to the posterior surface 40.

The number of spiral tracks can vary with the lens design, in the range of 1 to 200 tracks, and they can originate and end at any point or region within the lens surface. FIG. 1 shows four spiral tracks 24 extending from the edge of a central region 22 to the outer edge of the lens. The additional refractive power along spiral tracks can be inserted on the anterior, posterior or in both surfaces. The widths of the tracks can be constant or variable, and they can differ among tracks. These tracks can accommodate cycles of a periodic function that imparts optical power changes, or also fractions of a cycle, along any of the tracks independently. The boundaries between tracks can be contiguous or not. The spiral tracks can be defined by any variation of known spiral-curve functions as, for example, the Archimedean spiral, the Fermat spiral, the Lituus spiral, the Euler spiral, the logarithmic spiral (FIG. 3), the hyperbolic spiral, or be described by any other function in which the radius varies with the azimuthal angle (θ) in a spiral fashion. The general expression for a spiral function, in polar coordinates (r, θ), is given by Eq. 2, from which a particular class is presented in Eq. 3. Eq. 4 through Eq. 8 present specific variations that lead to different types of spirals. In the presented equations, a, b, β and θ are real numbers. Their values dictate how the radius increases with the azimuthal angle (θ).

General spiral expression:

$$r = a * f(\theta) + b, \quad \text{Eq. 2}$$

where, the function f(θ) as a power of theta is a common expression for spirals, as presented in Eq.2:

$$r = a * \theta^{\beta} + b \quad \text{Eq. 3}$$

- Archimedean spiral ($\beta = 1$):

$$r = a * \theta + b \quad \text{Eq. 4}$$

- Fermat Spiral $\left(\beta = \frac{1}{2}\right)$:

-continued $$r = a * \sqrt{\theta} + b \quad \text{Eq. 5}$$

∘ Lituus Spiral $\left(\beta = -\frac{1}{2}\right)$:

$$r = \frac{a}{\sqrt{\theta}} + b \quad \text{Eq. 6}$$

∘ Hyperbolic spiral ($\beta = -1$):

$$r = \frac{a}{\theta} + b \quad \text{Eq. 7}$$

∘ Logarithmic spiral $$r = a * e^{\bar{\beta} * \theta} + b \quad \text{Eq. 8}$$

The type of spiral pattern is defined by the parameter β from Eqs. 3 through 7, whereas the type of the spiral in Eq. 8 is defined by the exponential term, and not exclusively by the β value. The parameter β can be any real number in the range from −2 to 2. The parameter b of Eqs. 2 to 8 defines the radial distance from the center of the lens to the beginning of the spiral pattern, and the parameter a is related to the spiral width. In an intraocular lens, which is usually has a radius about 3 mm (diameter of 6 mm), the values of b can be any real number in the range from 0 to about 2.97 mm while the parameter a depends on the spiral type but, for the Archimedean spiral of one track, it is a real value bigger than 0 and usually smaller than 0.477 mm. The azimuthal angle (θ) is related to the number of turns of the spiral and can assume any real value in the range of 2 π to 400 π radians, which translates to 1 to 200 turns in one Archimedean spiral track. As the number of spiral tracks increases, the maximum number of turns decreases proportionally, e.g. 100 turns for a two-track spiral. This leads to a value of the parameter a that ranges from 0.477 mm to 2.39 μm, respectively. The maximum number of turns of the spiral can vary depending on the mathematical description of the spiral pattern and the number of tracks.

Once the type of spiral has been defined, a track is described as the region within two spiral lines (FIG. 2). The mathematical function describing the additional power distribution within a spiral track can differ from that of another track for the same lens surface.

Figure 8:
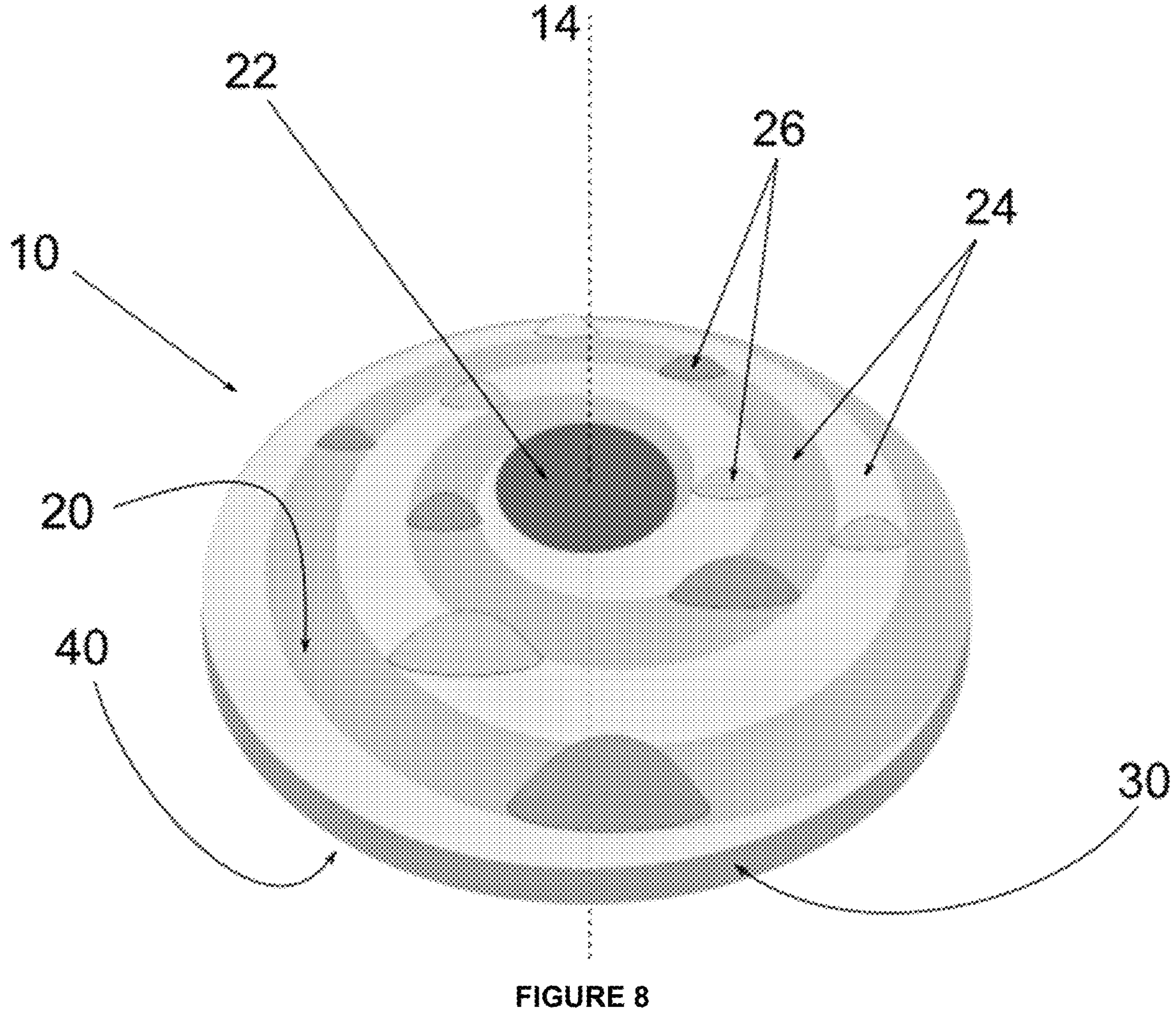
FIG. 8—Three-dimensional view of a lens embodiment 10 containing microlenses 26 distributed over a grid defined by two Archimedean spiral tracks 24.

The additional power variations can also be inserted on the spiral track by means of microlenses (FIG. 8). Microlenses are imaging elements on their own and can be combined to the base shape of the intraocular lens. As an imaging element on the surface of an intraocular lens, the microlens takes advantage of the plenoptic effect, in which the light field reaching it results from different angles than the light field reaching the base lens. This yields an image of an object laterally displaced from the image formed by the base lens. If the images are sufficiently overlapped and if the magnification is of the same order, this leads to a perception of an extended depth of focus. In plenoptic photography, a raster of microlenses is used and combined with an objective lens allowing the choice of the focal plane to be presented by post-processing the composite image.

The addition of microlenses also introduces extended design possibilities to fine tune the focal profile by bending rays at specific lens locations towards different longitudinal loci along any optical axis. These features and combinations thereof as presented in this invention enable the design of families of lenses with multifocal, enhanced monofocal or extended-depth-of-focus characteristics that are maintained or morphed across different pupil sizes.

Figure 9:
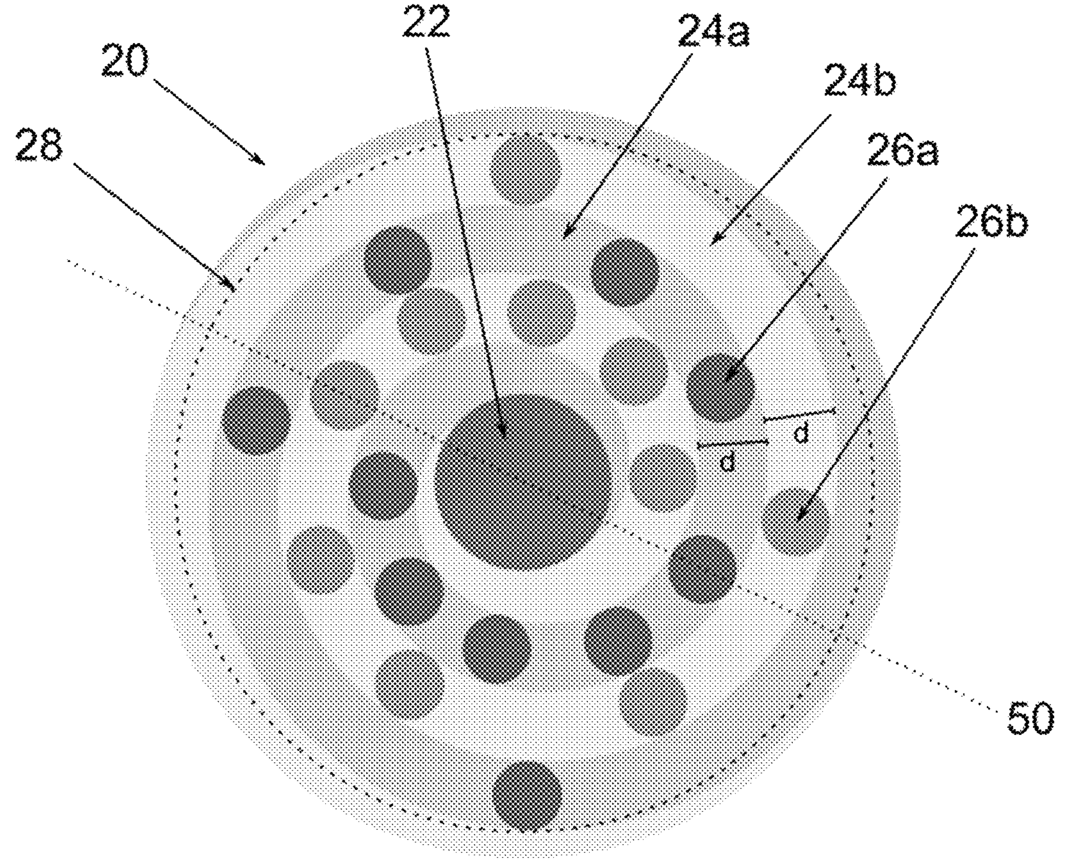
FIG. 9—Top view of a lens embodiment containing microlenses 26 distributed over a grid defined by two Archimedean spiral tracks 24.

The microlenses 26 are distributed along the spiral tracks 24, as illustrated in FIG. 9. The refractive power and shape of the microlenses 26 on one spiral track 24 can be different to that on another track.

The microlenses can be sparsely or contiguously distributed along the tracks, and can even overlap, as well as feature different refractive powers along the tracks. The microlenses can be spherical, aspheric, toric, sinusoidal, multi-aspheric, as defined in Eq. 10, or even described by means of a weighted sum of Zernike polynomial or Q polynomial terms. Each microlens can also be implemented as a diffractive optical element, for example, as a Fresnel lens. It can also have a convex or concave nature, and it can be made of the same material or refractive index of the base lens, or of a different material and refractive index. The profile of the microlenses can be totally or partially modulated by another function as Taylor series, Fourier series, Bessel functions, Jacobi polynomials or Lagrange polynomials, Zernike polynomials, or Seidel polynomials, or Q polynomials, or Noll polynomials, to guarantee a smooth transition between the microlens and the base surface, or between microlenses, avoiding detrimental diffractive or positive dysphotopic effects created by each microlens. Some aberration types, described by Zernike polynomials, or Seidel polynomials, or Q polynomials, or Noll polynomials, such as coma and spherical aberration, can be deliberately added to the microlenses (to some degree) in order to extend the overall depth of focus. The optical axes of the microlenses can be parallel to the optical axis of the intraocular lens, or they can be normal to the positions on the surface where they are located. However, to effectively impart tailored focal performance, they should be independently slanted at their most suitable angle.

The diameter of the microlens depends on the minimum horizontal resolution of the lathe (usually 300 nm or greater). Preferably, the diameter of the microlenses will have the same width as the spiral track on which it is inserted, which is usually around 50 μm (matching typical kinoform base width for diffractive lenses). The number of microlenses is theoretically not limited, being able to range from at least 2 microlenses per spiral track to infinity, if lateral overlap is considered. However, the amount of lateral overlap that still yields resolvable adjacent microlenses depends on the lateral accuracy and form accuracy of the manufacturing tool used. When the bases of contiguously distributed microlenses touch each other without overlapping and their diameter coincide with the width of the spiral track on which they are implemented, it is possible to obtain the maximum number of microlenses for the maximum number of turns for an intraocular lens with a 3 mm radius and two tracks defined by Archimedean spirals. The maximum number of microlenses in such a fashion on one track is calculated by the ratio of the length of the center of the spiral track to the width of the spiral track. The maximum number of turns depends on the diameter of the base lens and the minimum width of the spiral track $a_{MIN \cdot \pi}$, assuming that the spiral tracks start in the center of the base lens. The number of turns determines the maximum angle that is considered in the spiral length calculation. Therefore, for a microlens with 50 μm of diameter, a diameter of the base lens of 6 mm, and a maximum number of turns of 30, the maximum number of microlenses distributed over two Archimedean spiral tracks is 11,256 (eleven thousand two hundred and fifty-six).

Figure 10:
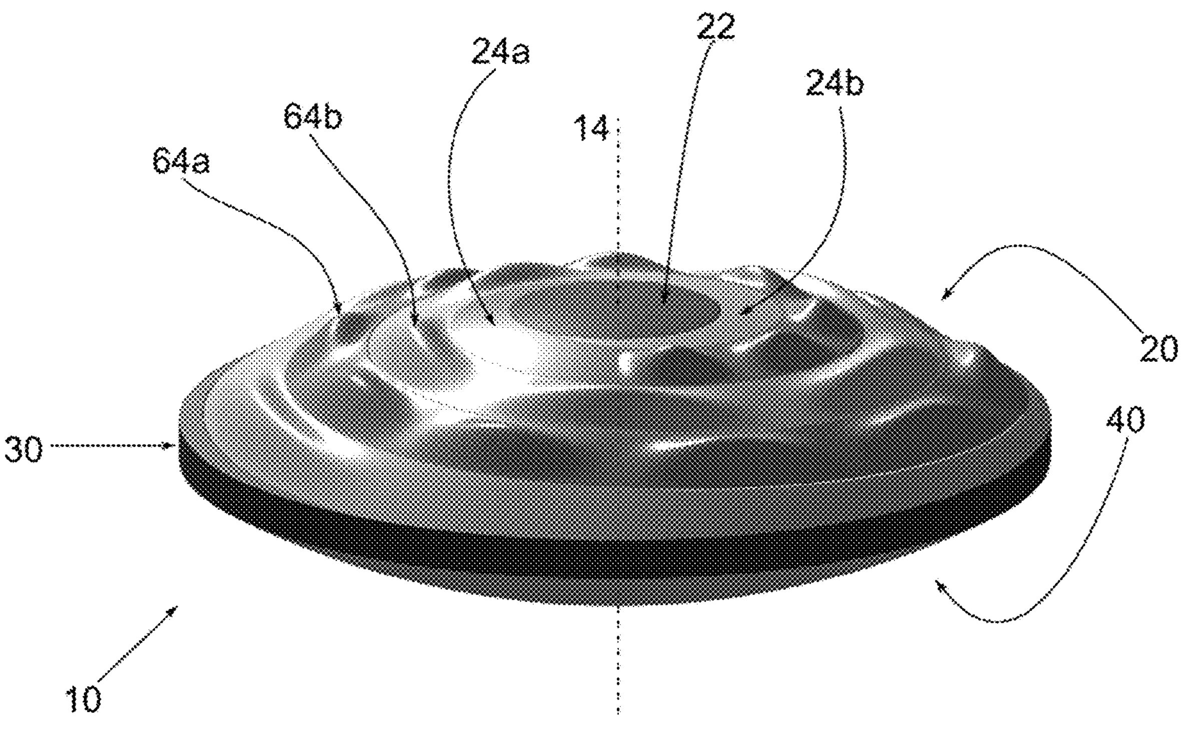
FIG. 10—Three-dimensional view of a lens 10 embodiment where the additional refractive power is implemented through periodic functions 64 (sinusoidal) distributed over a grid defined by two Archimedean spiral tracks 24. This embodiment also has a cylindrical body 30 inserted between the front and back surfaces of the lens.

The additional power can also be inserted through variations in the surface of the base lens following the spiral tracks both in relation to the radial position and the azimuth angle. FIG. 10 presents an embodiment of an intraocular lens 10, with an optical axis 14, a posterior surface 40, an anterior surface 20 both and a cylindrical section 30 connecting surfaces. On the anterior surface 20, two spiral tracks are defined, 24*a* and 24*b*, and there is a central circular area 22. Periodic functions are used to vary the optical power along the spiral tracks 24 both in the radial and azimuth directions. The periodic function can be any continuous function, e.g. a sinusoidal pattern or, more generally, a function described by a Fourier series. The frequency, amplitude, phase and duty cycle of the periodic variation can differ from one track to another. The frequency and amplitude can also vary within the same spiral track 24. The refractive power variation can be either positive or negative in relation to the reference optical power of the base lens. The periodic variation along the spiral tracks 24 are preferably inserted in such a way that the lens surface only presents smooth transitions. The maxima and minima of a more general periodic function can also be aligned to a direction other than parallel to the optical axis of the base lens or normal to the respective local position on the base-lens surface. The addition of a periodic function increases the number of lens design parameters, allowing for more versatility in fine tuning the base topology to attend to specific performance goals. The periodic functions yield to a variation on the refractive power allowing the customization of the visual acuity for different pupil sizes.

The periodic variation on the lens surface $z_{spiral}$ along one spiral track can, for instance, be defined as a sinusoidal pattern according to the Eq. 9.

$$z_{spiral} = f(r,\theta) = A\left\{\frac{\sin\left[f\cdot\theta - \frac{\pi}{2} - \phi\right] - 1}{2}\right\}\left\{\frac{\sin\left[\left(\frac{2\pi(r - r_{int})}{(r_{ext} - r_{int})}\right) - \frac{\pi}{2}\right] + 1}{2}\right\} \quad \text{Eq. 9}$$

Where A is the amplitude of the periodic function, f is the frequency that can vary with the azimuthal angle ($\theta$), $\phi$ is the phase of the azimuthal frequency, $r_{int}$ and $r_{ext}$ are, respectively, the internal and external radial boundaries of the spiral track that contains the periodic variation.

For an intraocular lens in the range from 4 to 10 mm of diameter, the amplitude value A can be either positive or negative, ranging from −20 μm to 20 μm, but preferably from −3 μm to 3 μm. The frequency f can be constant or can vary with the azimuthal angle, ranging from 0 cycles/turn until 100 cycles/turn. The phase $\phi$ can vary from 0 to 2 π radians and the azimuthal angle ($\theta$) can vary from 2 π to 200 π radians (or 1 to 100 turns). The parameters $r_{int}$ varies from 0 to 2.97 mm and $r_{ext}$ ranges from 0.03 mm to 3.0 mm.

The Eq. 9 ensures a smooth transition between the periodic variation on two adjacent spiral tracks and the base lens surface, avoiding deleterious diffractive effects due to abrupt steps.

The additional power following the spiral track can be deployed either to the lens anterior surface, or to its posterior surface, or to both surfaces, or it can even continuously transition between surfaces. The additional power can yield an extended depth of focus with a predicted preclinical monocular logMAR better than −0.2 (which equates to a visual acuity of 20/32 in Snellen chart) ranging from 0 D to 6.0 D on the plane of the lens. A multifocal lens can also be designed with additional focus larger than 6.0 D.

The base lens is determined by a modified aspheric surface. A simple aspheric surface can be defined by the Eq. 10, where the optical power of one surface of the lens depends on the lens curvature (c), and where k(r) is made constant, i.e. independent of the radial position r.

$$Z(r) = \frac{c \cdot r^2}{1 + \sqrt{1 - (1 + k(r))c^2 r^2}} \quad \text{Eq. 10}$$

Where r is the independent radial direction, c is the surface curvature associated with the radius of curvature $R_c$ ($c = 1/R_c$).

The curvature of each surface, anterior and posterior, can range from 0 (for a flat surface) to 0.4 $mm^{-1}$ (or 2.5 mm of radius of curvature) and the conic function k(r) can assume any real value in the range of −1,000 (minus one thousand) to 1,000 (one thousand). The curvatures of the anterior and posterior surfaces are calculated based on the expected reference power of the base lens, which is related to the refractive index of the lens and the central thickness. The reference power of commercial intraocular lenses usually ranges from 5 to 30 D.

The modified aspheric base lens, henceforth named multi-aspheric, can be designed by using a function to change the asphericity values of the base lens, k(r), making it a function that varies with the radial position. Eq. 10 can assume particular cases, such as a spherical surface (with k(r)=0), or as a simple aspheric surface (with k(r)=constant), where the sign and value of the constant determine which type of conic surface it describes. For example:

$-\infty < k < -1$: hyperbola $k = -1$: parabola $-1 < k < 0$: prolate ellipse $k = 0$: sphere $0 < k < \infty$: oblate ellipsef The base shape can also be concave, convex or plane and can be deployed on the anterior, posterior or on both surfaces of the lens.

The additional power variations along the spiral tracks can be deployed over the multi-aspheric base giving the lens greater versatility to tailor the desired visual acuity with the pupil variation.

Figure 11:
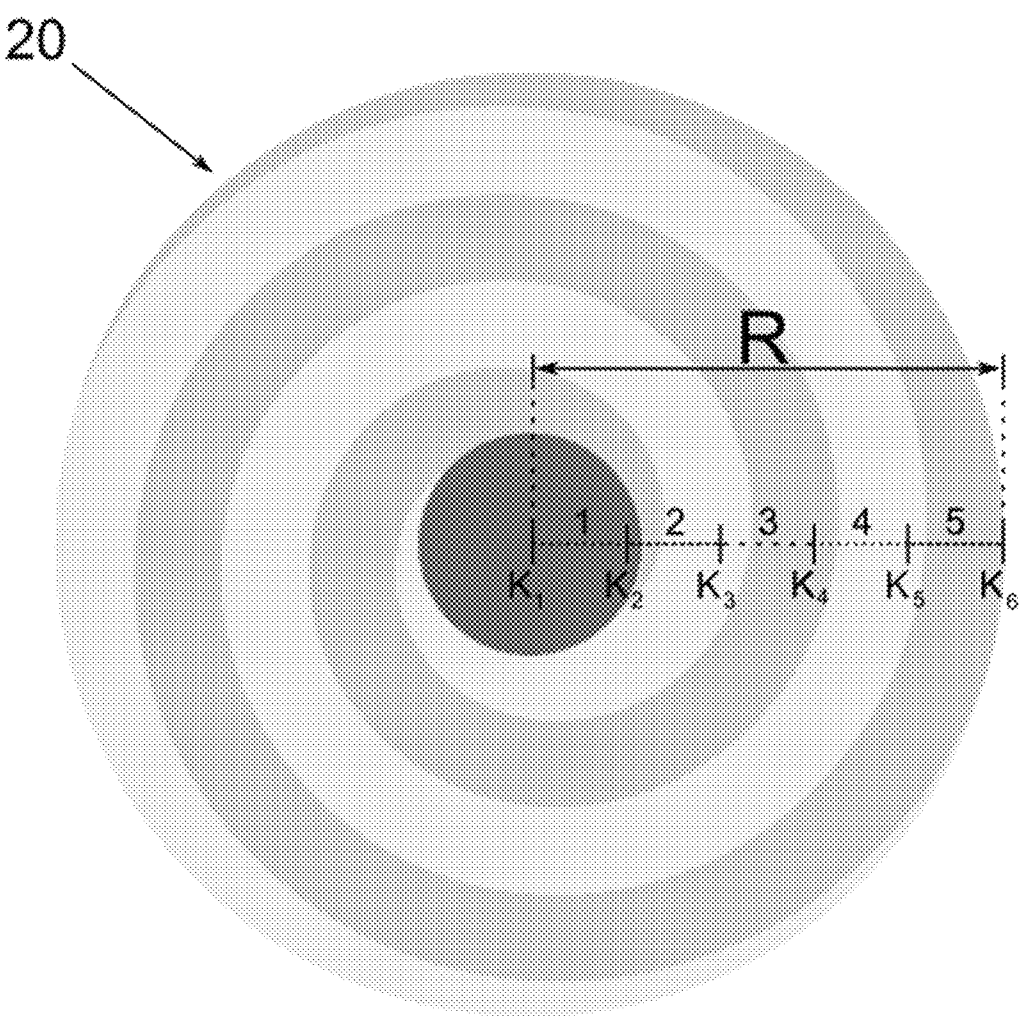
FIG. 11—Top view of a lens embodiment that exemplifies the definition of multi-aspheric segments that are dependent on the radial position.

The conic function k(r), determining the asphericity, can be formulated dividing the lens radius R in radial segments, as illustrated in FIG. 11. In this figure, the segments are numbered from 1 to 5 and have the same width. Each segment features a conic function that progresses from $K_n$, corresponding to the inner radius of the $n^{th}$ segment, to $K_{n+1}$, corresponding to the outer radius of the same segment. In the case illustrated in FIG. 11, the conic values vary from $K_1$ to $K_6$, and their respective values are affected by their respective radial positions on the lens surface. In an intraocular lens, the value for $K_n$ can be any real number ranging from −1,000 (minus one thousand) to 1,000 (one thousand).

The conic function k(r) between $K_n$ and $K_{n+1}$ can be defined as a linear function, as defined by Eq. 11.

$$k_n(r) = \left[\frac{(K_{n+1} - K_n)}{\Delta}\right][r - (n-1)\Delta] + K_n \quad \text{Eq. 11}$$

Where the radial position (r) varies from $\Delta\cdot(n-1)$ to $\Delta\cdot n$. Also, $\Delta$ is the width of each segment, given by the lens radius R divided by the number of segments N, and where n varies from 1 to N (in this case, N=5).

Figure 12:
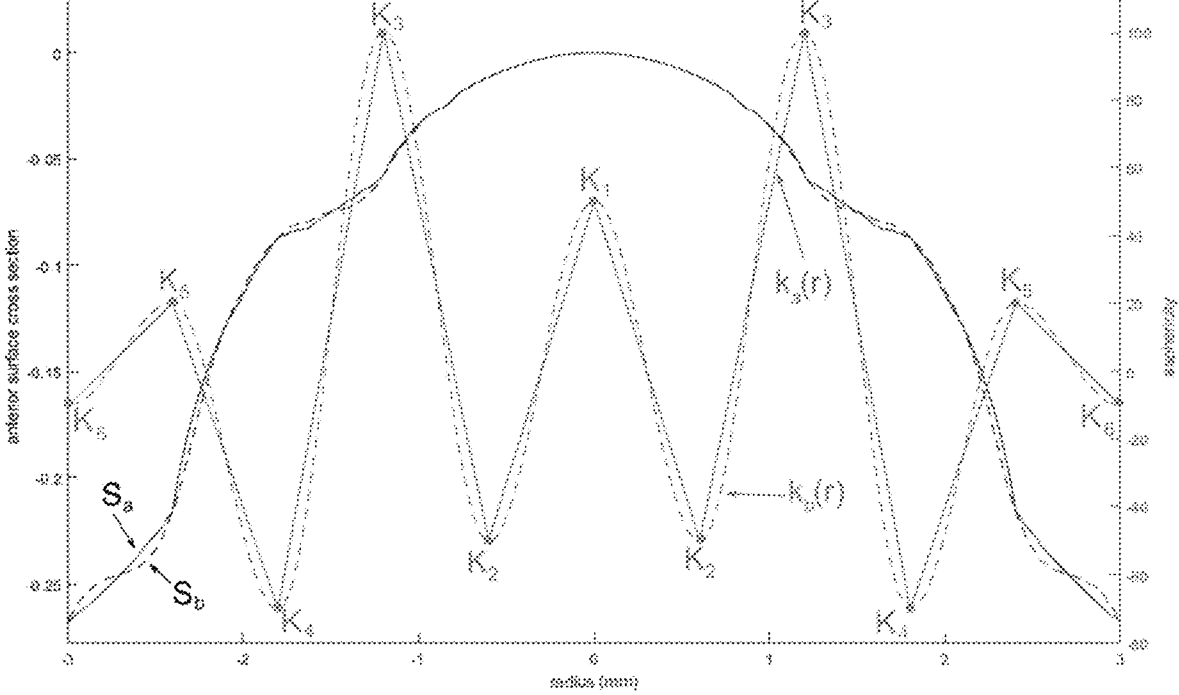
FIG. 12—Cross-section view of a multi-aspheric lens embodiment, showing the difference between the use of linear transitions (continuous lines) between conic values defined at specific radial positions and smooth transitions (dotted lines) between those specified conic values.

FIG. 12 presents an example of the cross section of the surface when Eq. 11 is used. Choosing $k(r)=k_a(r)$, which is given by a linear function between any two consecutive K values, at the edges of their respective segment, results in a varying but continuous conic surface $S_a$ across the lens. The linear function $k_a(r)$, however, does not ensure a smooth transition of the surface profile function $S_a$ between segments, depending on the respective K values at the intersections.

To ensure that the surface profile S is smooth at any transition, it is necessary to make the conic function k(r) continuous and differentiable. This can be accomplished using the function $k_b(r)$ defined as in Eq. 12.

$$k_n(r) = \beta_n K_n + (1-\beta_n)K_{n+1} \quad \text{Eq. 12}$$

$$\beta_n = \frac{\left\{1+\sin\left[\frac{\pi(r-(n-1)\Delta)}{\Delta}+\frac{\pi}{\Delta}\right]\right\}}{2} \quad \text{Eq. 13}$$

where the radial position (r) varies from $\Delta\cdot(n-1)$ to $\Delta\cdot n$. And $\Delta$ is the segment width, given by the lens radius R divided by the integer number of segments (N). Each segment is denoted by the sub-index n which varies from 1 to N. The maximum number of segments $N_{MAX}$ can be estimated if the lateral resolution $\sigma$ of the lathe is known and if the width of each segment $\Delta$ is made equal to $\Delta_{MIN}=\sigma$. For example, if the radius of the intraocular lens is R=3 mm and the horizontal resolution of the lathe $\sigma$ is 300 nm, it is possible to fabricate a maximum $N_{MAX}$=10,000 (ten thousand) segments of 300 nm width disposed along the radial direction. Hence, the number of segments N can range from 1 to 10,000 (ten thousand).

The results of the conic variation defined by Eq. 12 can be seen on the cross section curve $S_b$ of FIG. 12, which is smooth throughout its length.

Figure 6:
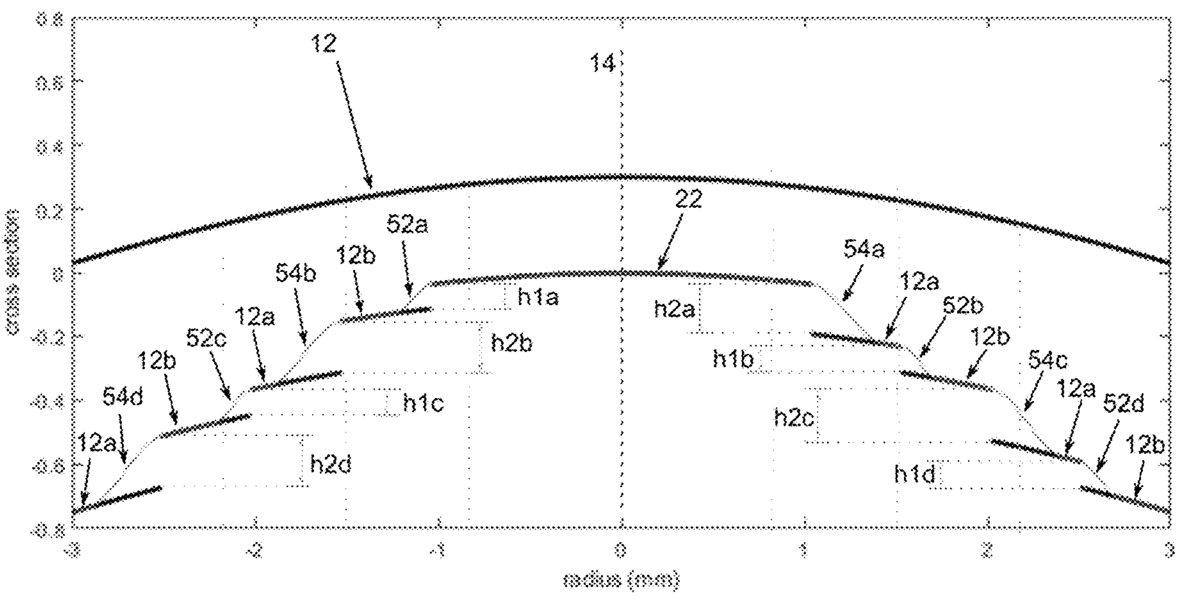
FIG. 6—A cross section showing a modification on the base lens surface topology, where its zones are defined by an Archimedean spiral grid and axially shifted in a helical fashion. It features smooth transitions between steps.
Figure 7A:
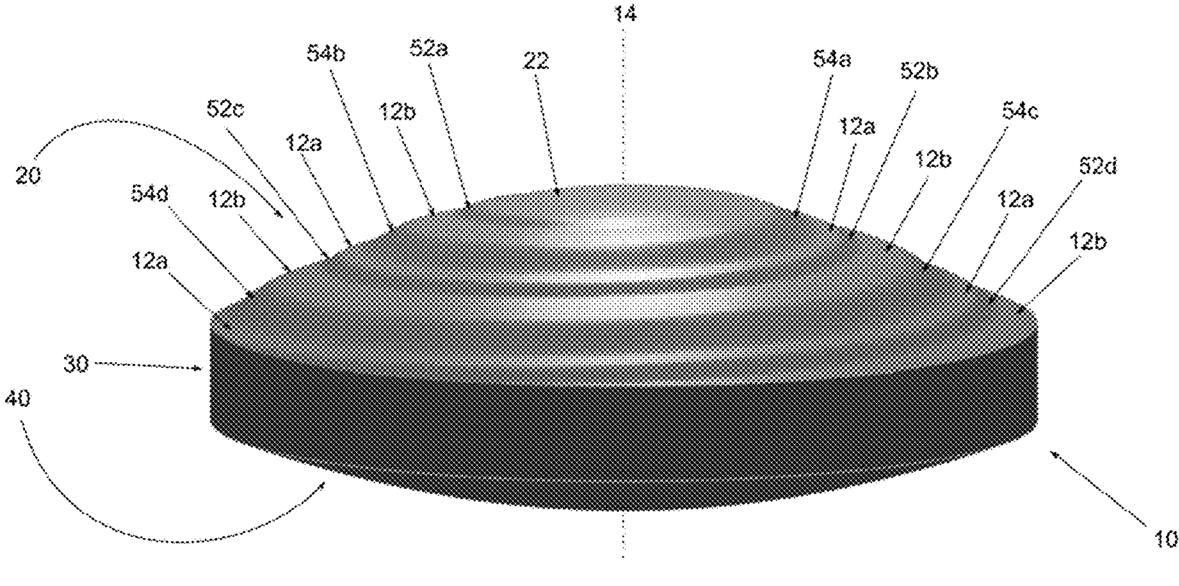
FIG. 7A—Three-dimensional view of a lens 10 embodiment with the helical step-like pattern on the spiral tracks, whose cross section is depicted in FIG. 6.
Figure 7B:
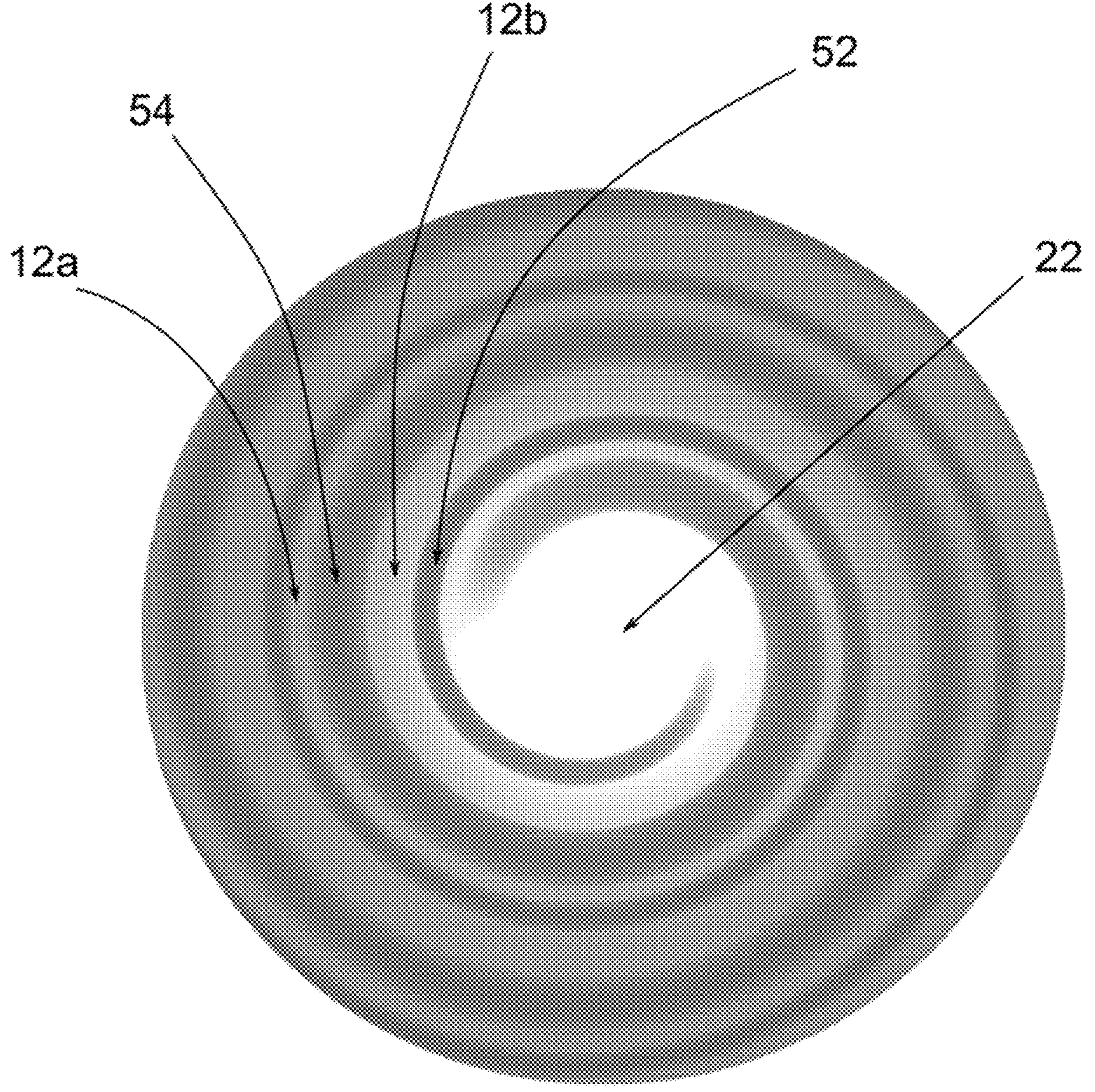
FIG. 7B—Top view of a lens embodiment with the helical step-like pattern on the spiral tracks, whose cross section is depicted in FIG. 6.

Regardless the mathematical function chosen to define the base surface, another attribute in the scope of this invention is the deliberate longitudinal helical shift of portions of the surface defined according to a spiral grid, whose resulting profile is in the fashion shown in FIG. 6, FIG. 7A and FIG. 7B, where the transition between steps can be made smooth and optically functional, conferring additional power to those already effected by the base profile. The transition function can follow a linear function, or a continuous function described by a Taylor series, a Fourier Series, a Bessel function, Jacobi polynomials or Lagrange polynomials, but it is preferably defined by a smooth truncated sinusoidal function. This transition uses a percentage of the radial dimension of the spiral tracks and is designed to confer a different optical power to the lens, other than that of the base surface. The percentage of the transition can vary from 0% to 100% of the spiral track width, with 0% meaning an abrupt transition while 100% yields the smoothest transition. The power variation depends on the chosen function, the transition width and the shift height. This smooth stepwise shift combines the advantages of a spiral pattern to additional power induction without deleterious diffractive effects caused by abrupt steps. The amplitude of the step in one track can be the same all over the spiral track or can vary along the track. In addition, the amplitude of the step in consecutive tracks do not need to be the same. Besides, microlenses, periodic functions and any other secondary function can be implemented along the tracks defined by the spiral grid. The minimum amplitude of the longitudinal axial shift is limited to the vertical resolution of the lathe, usually having a value of 100 nm or greater. In an intraocular lens, the shift amplitude is not expected to exceed 1 mm.

All topological elements described above can be manufactured by means of fabrication methods already widely used in the ophthalmic industry, based on diamond turning, casting, hot stamping, injection molding or lithographic pattern etching. State-of-the-art methods such as RIS (Refractive-Index Shaping) by a femtosecond laser, for example, could also be employed to generate refractive power variations along spiral tracks in the realm of Laser Induced Refractive Index Change (LIRIC). Because most of the features are rotationally asymmetric in relation to the lens optical axis, a lathe with asymmetric capabilities is required if turning is intended. The minimum feature dimensions to be designed depend on the specific precision of each piece of equipment, or combination of equipment, employed in the manufacturing process.

As for the material, all the elements aforementioned can be readily manufactured using any of the standard materials already employed in the ophthalmic industry, rigid or foldable, hydrophobic or hydrophilic, as methacrylate-based and silicone materials, including PMMA, collamers, macromers, hydrogels and acrylates. In uses other than ophthalmic, the lenses herein proposed can make use of a wider range of both polymers and glasses.

DESCRIPTION OF THE PREFERRED EMBODIMENTS OF THE INVENTION

The embodiments herein presented are not intended to act as restrictions, but rather to exemplify the characteristics of the invention.

Embodiment 1

One preferred embodiment aims at an extended-depth-of-focus intraocular lens based on an aspheric anterior surface remodeled by a step-like pattern in a spiral fashion with smooth transition between the consecutive shifted partitions, which results in a refractive power variation from far to near distance, promoting a contrast performance tailored to different pupil sizes.

FIG. 7A presents an intraocular lens 10, with an aspheric posterior surface 40 and an anterior surface 20 designed in a step-like helicoidal pattern about the lens optical axis 14. The anterior surface is mapped by a grid defined by two juxtaposed Archimedean spiral tracks 12*a* and 12*b*, with each spiral encompassing two full cycles (number of turns). The anterior surface is a pop-up version of the base aspheric surface where its partitions, delimited by the spiral grid, are axially shifted with respect to the partitions on adjacent tracks, forming a helicoidal structure. Besides, to avoid abrupt steps between adjacent spiral tracks and providing the desired refractive power variation, a transition region is defined by an incomplete period of a sinusoidal function, as presented in Eq. 14, guaranteeing a smooth surface change. FIG. 6 shows one cross section of the anterior aspheric surface modified as described above. The transitions are labelled as 52 and 54, indicating a transition from the spiral track 12*a* to 12*b*, and one from spiral 12*b* to 12*a*, respectively. The step heights are indicated by h1*a* through h1*d* and h2*a* through h2*d*. In the same cross section the transition profile for a given track is indicated by 52*a* through 52*d*, and 54*a* through 54*d*, depending on the respective spiral track and on its radius. The transition width occupies part of the track to which it transitions. In this embodiment, the transition of step 54*a-d* on track 12*a* is wider than that of transition step 52*a-d* on track 12*b*. The transition of step 54*a-d* occupies 70% of the spiral track width, while the transition 52*a-d* occupies only 35% of the spiral track width.

In this embodiment, the transition function is defined by the Eq. 14.

$$z_{step} = h_n(\theta)\frac{\left[\sin\left(\alpha\pi + \frac{\pi}{2}\right) + 1\right]}{2} \quad \text{Eq. 14}$$

Where $h_n(\theta)$ is the amplitude of the step in the transition of track n to n+1, which can be constant and is bigger than 0 and smaller than 1 mm, and a is a value in the range of 0 to 1 related to the percentage of the width used in the transition and truncates the sinusoidal function, according to Eq. 15.

$$\alpha = \frac{r - r_{int}}{100 \cdot P(\theta) \cdot (r_{ext} - r_{int})} \quad \text{Eq. 15}$$

Where $r_{int}$ and $r_{ext}$ are the internal and external limits of the spiral track in the radial position and P(θ) is the percentage of the track width used in the transition, which can vary from 0 to 100% of the spiral track width, with r limited to the transition region. For an intraocular lens with 3 mm of radius, the parameters $r_{int}$ varies from 0 to 2.97 mm and $r_{ext}$ ranges from 0.03 mm to 3.0 mm.

The shifted heights are constant between a certain spiral track and its adjacent one. This pattern extends from the edge of the central area 22, which has 0.55 mm or radius, to the border of the lens. The heights h1*a* through h1*d*, between spiral tracks 12*a* and 12*b*, have a constant value that is half the one defined for h2*a* through h2*d*, with respect to the transition between the spiral tracks 12*b* and 12*a*, as can be seen in the profile view in FIG. 6. To avoid abrupt changes on the lens surface in the first 180 degrees of the first turn of each track spiraling from the central region 22, the shifted height there varies following a continuous function from zero to the corresponding defined value fixed for in-between spiral tracks.

In FIG. 7B, it is possible to notice the overall result of having a step-like Archimedean spiral with two different transition regions. Although the spiral steps have the same width across the entirety of the optical zone, the superposition of the transition regions modifies the surface, so it appears as being an Archimedean spiral with four tracks of different widths.

The minimum amplitude of the longitudinal axial shift is limited to the vertical resolution of the lathe, usually around 100 nm. In an intraocular lens, the shift amplitude is not expected to exceed 1 mm. The shifted transition can extend outwards from the central area 22 until the border of the lens, as presented in FIG. 7A, or it can be limited by a predefined circle smaller than the lens diameter. The shifted height on one spiral track can be fixed or can depend on the azimuthal angle and the radial position following a continuous function to avoid abrupt transitions and diffractive effects. This continuous function can be described by a Taylor series, a Fourier series, Bessel functions, Jacobi polynomials or Lagrange polynomials.

This transition uses a percentage of the radial dimension of the spiral tracks, which can be dependent of the azimuthal angle θ, and is designed to confer a different optical power to the lens, other than that of the base surface. The percentage of the transition can vary from 0% to 100% of the spiral track, with 0% meaning an abrupt transition while 100% yields the smoothest transition.

The transition area confers the additional power to the base lens that can be positive or negative in relation to the reference power. The step-like pattern can be deployed on the anterior surface, posterior surface, or on both surfaces, or even inside the lens body.

The number of turns is in the range of 1 to 200 (with the azimuthal angle θ varying from 2 π to 400 π radians). Also, the spiral pattern can follow any of those defined by Eqs. 2 to 8. The radius of the circular central area from which the spiral pattern evolves to the border can vary from 0 mm to 2.97 mm, in an intraocular lens of 3 mm of radius. The number of tracks on the spiral pattern is not fixed and can vary from 1 to 200.

A variation of this embodiment encompasses all features of the aforementioned embodiment and include a periodic function on azimuthal and radial directions can be imparted to the lens surface on the same spiral tracks of the step-like pattern or following its own spiral track. The frequency, amplitude, phase and duty cycle of the periodic variation can differ from one track to another. The periodic function can be any continuous function, e.g. a sinusoidal pattern or, more generally, a function described by a Fourier series. The periodicity and amplitude can also vary on the same spiral track. The refractive power variation can be either positive or negative in relation to the reference optical power of the base lens. The periodic variation along the spiral tracks are preferably inserted in such a way that the lens surface keeps smooth. The maxima and minima of a more general periodic function can also be aligned to a direction other than parallel to the optical axis of the base lens or normal to the respective local position on the base-lens surface.

The periodic function along the spiral track can be defined by the sinusoidal pattern, as described in Eq. 9. In an intraocular lens of 6 mm of diameter, the amplitude value A can be either positive or negative, ranging from −20 μm to 20 μm, but preferably from −3 μm to 3 μm. The frequency f can be constant or can vary with the azimuthal angle, ranging from 1 cycles/turn until 100 cycles/turn. The phase ϕ can vary from 0 to 2 π radians and the azimuthal angle (θ) can vary from 2 π to 200 π radians (or 1 to 100 turns). The parameters $r_{int}$ varies from 0 to 2.97 mm and $r_{ext}$ ranges from 0.03 mm to 3.0 mm.

Another variation of the previous embodiment comprises all the aforementioned features and also has microlenses placed on the spiral tracks or following a different spiral, which can have different formats, number of tracks and number of turns. The microlenses can be sparsely or contiguously distributed along the tracks, as well as feature different refractive powers along the tracks. The microlenses can be spherical, aspheric, multi-aspheric, toric, sinusoidal or even described by means of a weighted sum of Zernike polynomial or Q polynomial terms. Each microlens can also be implemented as a diffractive optical element, for example, as a Fresnel lens. It can also have a convex or concave nature, and it can be made of the same material or refractive index of the base lens, or of a different material or refractive index. The profile of the microlenses can be totally or partially modulated by another function as Taylor series, Fourier series, Bessel functions, Jacobi polynomials or Lagrange polynomials, Zernike polynomials, or Seidel polynomials, or Q polynomials, or Noll polynomials, to guarantee a smooth transition between the microlens and the base surface, or between microlenses, avoiding detrimental diffractive or positive dysphotopic effects by each microlens. A proper degree of some aberration types, described by Zernike polynomials, or Seidel polynomials, or Q polynomials, or Noll polynomials, as coma and spherical aberration, can be deliberately added to the microlenses to extend its depth of focus. The optical axes of the microlenses can be parallel to the optical axis of the intraocular lens, or they can be normal to the positions on the surface where they are located. However, to effectively impart tailored focal performance, they should be independently slanted at their most suitable angle.

The surface of each microlens can be described by the same equation as that of an aspheric surface (Eq. 10). The diameter of the microlens depends on the minimum horizontal resolution of the lathe (usually 300 nm or greater). Preferably, the diameter of the microlenses will have the same width as the spiral track on which it is inserted, which is usually around 50 μm (matching typical kinoform base width for diffractive lenses). The number of microlenses is theoretically not limited, being able to range from at least 2 microlenses per spiral track to infinity, if lateral overlap is considered. However, the amount of lateral overlap that still yields resolvable adjacent microlenses depends on the lateral accuracy and form accuracy of the manufacturing tool used. When the bases of contiguously distributed microlenses touch each other and their diameter coincide with the width of the spiral track on which they are implemented, it is possible to obtain the maximum number of microlenses for the maximum number of turns for an intraocular lens with a 3 mm radius and two tracks defined by Archimedean spirals. The maximum number of microlenses in such a fashion on one track is calculated by the ratio of the length of the center of the spiral track to the width of the spiral track. The maximum number of turns depends on the diameter of the base lens and the minimum width of the spiral track $a_{MIN} \cdot \pi$ (assuming that the spiral tracks start in the center of the base lens). The number of turns determines the maximum angle that is considered in the spiral length calculation. Therefore, for a microlens with 50 μm of diameter, a diameter of the base lens of 6 mm, and a maximum number of turns of 30, the maximum number of microlenses considering two spiral tracks is 11,256 (eleven thousand two hundred and fifty-six).

The anterior and posterior base lens surface can be defined by a multi aspheric surface, which could also consider a toric component for astigmatism compensation. Any of these cases can also feature microlenses or periodic power variations along spiral tracks as described previously.

Power modifications can also be added to the previous embodiments by means of diffractive topologies such as Fresnel and diffractive optical elements (DOE), either binary or multilevel.

The plethora of variations herein described may be used to design lenses for different focal and image-contrast performances, where the target could be either a multifocal, or an enhanced monofocal, or an extended depth-of-focus lens, or even a lens whose characteristic target performance changes with the pupil diameter.

Embodiment 2

Another preferred embodiment aiming an extended-depth-of-focus lens is based on the microlenses placed along two tracks of Archimedean spiral in a multi aspheric anterior surface promoting a contrast performance tailored to different pupil sizes.

FIG. 8 shows an intraocular lens 10 formed by an anterior surface 20 and a posterior surface 40, disposed about an optical axis 14, and a cylindrical body 30 connecting both surfaces. The base topology of the anterior surface 20 is a multi-aspheric surface, where each aspheric region follows a shape according to Eq. 12 and the posterior surface is a conventional aspheric surface with a single conic constant. On the anterior surface 20, two Archimedean spiral tracks 24 comprising two complete cycles are defined, along which microlenses 26 are distributed. The anterior surface 20 is designed as a multi aspheric base with a central region 22 from whose outer edge the spiral tracks 24 evolve outwards. The reference refractive power of the base lens depends on the curvature of the anterior 20 and posterior 40 surfaces, the refractive index of the material and the central thickness of the lens.

The depth of focus from far distance (0 D) to intermediate distance (about 2 D on the lens reference surface) is provided by the variation of the asphericity in a multi aspheric base surface, following Eq. 12. The microlenses **26*a* and 26*b*, shown in FIG. 9, contribute with different additional powers, in such a way that each spiral track, 24*a* and 24*b*, are designed for different focal distance from intermediate to near focus in the range of 2 D to 3.5 D on the lens reference surface. Both spiral tracks 24*a* and 24*b* have the same width d, which corresponds to the base diameters of the microlenses 26*a* and 26*b*. The microlenses 26*a* along the spiral track 24*a* are more spaced out as the spiral track evolves from the central region to the periphery of the lens. The number of microlenses 26 disposed on the spiral tracks is limited by the central region 22, the external reference circle 28, and the diameter of the microlenses. The microlenses 26*b* along the spiral track 24*b* are distributed in the same manner as those in spiral track 24*a*. Since the distribution along each spiral track 24 is symmetrical in relation to any meridian passing through the center of the lens, as the pupil increases, an additional power promoted by the microlenses in one spiral track, along a given meridian 50**, is imparted by the microlenses of the other spiral track.

The additional power of the microlenses 26 either on the same spiral track or on different tracks does not need to be equal. The additional power of each microlens 26 in one track can vary in any fashion along a spiral track. Two adjacent microlenses 26 can touch and even overlap, if desired. Besides, the distance between two consecutive microlenses 26 along a given spiral track does not need to be constant.

The number of cycles of the spiral pattern is in the range from 1 to 100 but is preferably in the range from 1 to 60, since it can vary, and the maximum number is limited by the minimum manufacturable diameter d of the base of the intended microlenses 26, which depends on the minimum-feature precision and repeatability of the manufacturing process used. The microlenses 26 can be sparsely or contiguously distributed along the tracks, as well as feature different refractive powers along the tracks. The microlenses can be simple aspheric, spherical, multi-aspheric, toric, sinusoidal or even described by means of a weighted sum of Zernike polynomial or Q polynomial terms. Each microlens can also be implemented as a diffractive optical element, for example, as a Fresnel lens. Each microlens can also have a convex, or concave nature, and can be made of the same material or refractive index of the base lens, or of a different material or refractive index. The profile of the microlenses 26 can be totally or partially modulated by another function as Taylor series, Fourier series, Bessel functions, Jacobi polynomials or Lagrange polynomials, Zernike polynomials, or Seidel polynomials, or Q polynomials, or Noll polynomials, to guarantee a smooth transition between the microlens and the base surface, or between microlenses, avoiding detrimental diffractive or positive dysphotopic effects by each microlens 26. A proper degree of some aberration types, described by Zernike polynomials, or Seidel polynomials, or Q polynomials, or Noll polynomials, can be deliberately added to the microlenses 26 to extend its depth of focus. The optical axes of the microlenses 26 can be parallel to the optical axis of the intraocular lens, or they can be normal to the positions on the surface where they are located. However, to effectively impart tailored focal performance, they should be independently slanted at their most suitable angle.

The number of turns is in the range of 1 to 100 (with the azimuthal angle $\theta$ varying from $2\pi$ to $200\pi$ radians). Also, the spiral pattern can follow any of those defined by Eqs. 2 to 8. The radius of the circular central area from which the spiral pattern evolves to the border can vary from 0 mm to 2.97 mm, in an intraocular lens of 3 mm of radius. The number of tracks on the spiral pattern is not fixed and can vary from 1 to 100.

The modified multi-aspheric base lens and the microlenses can be implemented on the anterior, posterior or both surfaces of the lens. Also, the anterior or posterior surfaces of the lens can consider a toric component to correct for astigmatism.

The number of predefined asphericity values in the multi-aspheric base surface is not fixed, hence the number of segments in between is not either. The greater the number of segments chosen, the better the adjustment of the contrast performance tailored to different pupil sizes. The multi-aspheric base lens can follow Eqs. 10, 11 and 12, but are preferably described by the Eq. 12, which yields smooth transitions over the lens surface. In an intraocular lens of 3 mm of radius, the conic values can be any real number ranging from −1,000 (minus one thousand) to 1,000 (one thousand).

The use of varying aspheric functions defined within radial segments enables the design of a lens that features both high contrast images for different pupil sizes and a focal range that preferably extends from distant to intermediate vision, but that could cover any other suitable range.

The additional deployment of microlenses along spiral tracks to the design, combined to the multi-aspheric base surface, extends the enhanced focal performance towards near vision, customizable to different pupil sizes. These two strategies offer multiple design parameters, and their composite effect renders lenses with extended depth of focus, where vision acuity can be designed to either be approximately constant throughout the extended vision range and pupil openings or to prioritize specific distances for different pupil sizes.

In another embodiment, a periodic function on azimuthal and radial directions following spiral tracks can be imparted to the multi-aspheric base surface of the lens. The extended-depth-of-focus is promoted by a combination of both structures. The frequency, amplitude, phase and duty cycle of the periodic variation can differ from one track to another. The periodic function can be any continuous function, e.g. a sinusoidal pattern or, more generally, a function described by a Fourier series. The periodicity and amplitude can also vary on the same spiral track. The refractive power variation can be either positive or negative in relation to the reference optical power of the base lens. The periodic variation along the spiral tracks is preferably inserted in such a way that the lens surface keeps smooth. The maxima and minima of a more general periodic function can also be aligned to a direction other than parallel to the optical axis of the base lens or normal to the respective local position on the base-lens surface. The embodiment can also have microlenses placed following the same spiral track or in a spiral fashion of its own.

The periodic function along the spiral track can be defined by the sinusoidal pattern, as described in Eq. 9. In an intraocular lens of 6 mm of diameter, the amplitude value A can be either positive or negative, ranging from −20 μm to 20 μm, but preferably from −3 μm to 3 μm. The frequency f can be constant or can vary with the azimuthal angle, ranging from 1 cycles/turn until 100 cycles/turn. The phase $\phi$ can vary from 0 to $2\pi$ radians and the azimuthal angle ($\theta$) can vary from $2\pi$ to $200\pi$ radians (or 1 to 100 turns). The parameters $r_{int}$ varies from 0 to 2.97 mm and $r_{ext}$ ranges from 0.03 mm to 3.0 mm.

The spiral pattern can follow any of those defined by Eqs. 2 to 8. The radius of the circular central area from which the spiral pattern evolves to the border can vary from 0 mm to 2.97 mm, in an intraocular lens of 3 mm of radius. The number of tracks on the spiral pattern is not fixed and can vary from 1 to 100.

Power modifications can also be added to the previous embodiments by means of diffractive topologies such as Fresnel and diffractive optical elements (DOE), either binary or multilevel.

The plethora of variations herein described may be used to design lenses for different focal and image-contrast performances, where the target could be either a multifocal, or an enhanced monofocal, or an extended-depth-of-focus lens, or even a lens whose characteristic target performance changes with the pupil diameter.

Embodiment 3

Another preferential embodiment aims at an extended-depth-of-focus lens with contrast performance tailored to different pupil sizes with refractive power ranging from distant to near focus, where microlenses are disposed along four Archimedean spiral tracks defined over an aspheric anterior surface. The posterior surface is aspheric.

FIG. 1 illustrates a surface with four spiral tracks 24, a central aspheric region 22 and an outer circular boundary 28 that is smaller than the outer physical dimension of the lens. In this embodiment, the microlenses are limited between the central and the outer region and are symmetrically distributed and equally spaced along each track. It means that the microlenses are laid in such a way that their positions are the same if the lens is rotated by 90 degrees, regardless of its optical power. The additional powers of the microlenses are defined such that they contribute to the power range of the base lens, extending the depth of focus from far to near distance. The distance between microlenses and their power distribution allows the adjustment of the image contrast for different pupil apertures.

The number of spiral tracks, the number of turns and the number of microlenses are not fixed, neither are the additional power distribution and the positions of the microlenses. Also, the spiral pattern can follow any of those defined by the Eqs. 2 to 8.

The number of turns is in the range of 1 to 100 (with the azimuthal angle $\theta$ varying from $2\pi$ to $200\pi$ radians). Preferably, the number of turns has a maximum value of 60 turns for microlenses of 50 μm of diameter and a base lens with a diameter of 6.0 mm for an Archimedean spiral of one track. These dimensions lead to a maximum number of microlenses equal to 11,256 (eleven thousand two hundred and fifty-six). The number of tracks on the spiral pattern is not fixed and can vary from 1 to 100. Their combined additional refractive power ranges from 0 to 6.0 D. The positions of the microlenses depend on the length and width of the spiral tracks, given the finite dimensions of the base lens (typically 6.0 mm).

The microlenses can be spherical, aspheric, multi-aspheric, toric, sinusoidal or even described by means of a weighted sum of Zernike polynomial or Q polynomial terms. Each microlens can also be implemented as a diffractive optical element, for example, as a Fresnel lens. It can also have a convex, concave nature, and can be made of the same material or refractive index of the base lens, or of a different material or refractive index. The profile of the microlenses can be totally or partially modulated by another function as Taylor series, Fourier series, Bessel functions, Jacobi polynomials or Lagrange polynomials, Zernike polynomials, or Seidel polynomials, or Q polynomials, or Noll polynomials, to guarantee a smooth transition between the microlens and the base surface, or between microlenses, avoiding detrimental diffractive or positive dysphotopic effects by each microlens. A proper degree of some aberration types, described by Zernike polynomials, or Seidel polynomials, or Q polynomials, or Noll polynomials, such as coma and spherical aberration, can be deliberately added to the microlenses to extend its depth of focus. The optical axes of the microlenses can be parallel to the optical axis of the intraocular lens, or can be normal to the positions on the surface where they are located. However, to effectively impart tailored focal performance, they should be independently slanted at their most suitable angle.

The outer 28 and the inner areas 22, present in FIG. 1, can also vary as needed to accomplish the desired contrast performance at different pupil sizes. Using an Archimedean spiral model, the diameter of the microlenses is fixed. When another type of spiral track is used as, for example, a logarithmic spiral illustrated in FIG. 3, the diameter of a given microlens, if defined by the track width, depends on its position on the lens surface, as the spiral track width increases with the azimuthal angle.

Another variation of the previous embodiment comprises all the aforementioned features (illustrated in FIG. 10) and also aims at an extended-depth-of-focus lens. The intraocular lens 10 is formed by an anterior aspheric base surface 20 and a posterior aspheric 40 surface, disposed about an optical axis 14, and a cylindrical body 30 connecting both surfaces. The anterior surface 20 has a circular central area 22 from whose outer edge two Archimedean spiral tracks 24, with each one contemplating two complete cycles, evolve outwards. Following the spiral tracks 24, positive and negative power variations are introduced on the base lens surface by means of a sinusoidal periodic function 64, both in the radial and azimuthal directions, as defined in Eq. 9. This assures a smooth transition on the base surface. The oscillation frequency along the spiral track 24*a*, following the azimuthal angle, is twice that on the spiral track 24*b*. The periodic functions 64 on both spiral tracks 24 have the same amplitude and phase. The maxima and minima of the periodic functions 64 have the same direction of the optical axis 14.

In additional variations of the previous embodiment, the frequency, amplitude, phase and duty cycle of the periodic variation 64 can differ from one track to another. For instance, the periodicity, i.e. frequency, preferably ranges from 1 cycle/turn to 100 cycles/turn, the phase ranges from 0 to 2 $\pi$ radians, and the amplitude depends on the vertical resolution of the lathe (typically 100 nm).

The periodic function can be any continuous function other than sinusoidal, e.g. a function described by a Fourier series. The periodicity and amplitude can also vary on the same spiral track 24. The refractive power variation can be either positive or negative in relation to the reference optical power of the base lens. The periodic variation 64 along the spiral tracks 24 is preferably inserted in such a way that the lens surface keeps smooth. The maxima and minima of a more general periodic function can also be aligned to a direction other than parallel to the optical axis of the base lens or normal to the respective local position on the base-lens surface.

Another variation of the previous embodiment comprises all aforementioned features with the inclusion of a similar periodic function variation along spiral track but also deploy microlenses, which are distributed following the same tracks of periodic function or can have their own spiral model. Either way, the microlenses and the periodic function can be overlapped.

Another variation of the previous embodiment comprises all aforementioned features with the inclusion of a multi-aspheric lens surface with power variation on azimuth and radial periodic variation can be designed in a step-like helicoidal pattern about the lens optical axis, with smooth transition between shifted points.

Power modifications can also be added to the previous embodiments by means of diffractive topologies such as Fresnel and diffractive optical elements (DOE), either binary or multilevel.

The plethora of variations herein described may be used to design lenses for different focal and image-contrast performances, where the target could be either a multifocal, or an enhanced monofocal, or an extended depth-of-focus lens, or even a lens whose characteristic target performance changes with the pupil diameter.

The use of the additional power variation along spiral tracks, whether based on microlenses, periodic functions with azimuthal and radial variation, smooth transitions between shifted helicoidal surfaces or a combination of those, provides many parameters to be adjusted to achieve the desired contrast on the retinal image tailored to different pupil sizes or the visual needs of certain patient classes according to their respective functional profiles.

All the embodiments can include haptics of any type, even though it is not mentioned herein.

REFERENCE CHARACTERS $\Phi_{IOL}$ Base lens refractive power
$n_{IOL}$ Refraction index of the intraocular lens
$n_{aq}$ Refraction index of the aqueous humor
$n_{vit}$ Refraction index of the vitreous humor
$R_{ant}$ Radius of curvature of the anterior surface
$R_{pos}$ Radius of curvature of the posterior surface
$t_{IOL}$ Central thickness of the intraocular lens
r Radial position coordinate
$\theta$ Azimuthal angle coordinate
a Parameter related to the thickness of a given spiral track
b Parameter related to the radial starting point of a given spiral track
$\beta$ Parameter related to the azimuthal rate of progression of any type of spiral
$z_{spiral}$ Sinusoidal function following a spiral grid
A Amplitude
f Frequency
$\phi$ Phase
$r_{int}$ Internal radial boundary of a given spiral track
$r_{ext}$ External radial boundary of a given spiral track Z(r) Function defining a lens or microlens profile as a function of the radial coordinate c Curvature associated with the radius of curvature of a given surface of a lens or a microlens k(r) Function defining the asphericity (conic value) as a function of the radial coordinate $k_n(r)$ Function defining the asphericity (conic value) that depends on a finite set of conic values $\beta_n$ Smooth transition function between two asphericity values Δ Parameter that controls the radial width of a given aspheric segment (multi-aspheric)

$z_{step}$ Transition function between steps in a spiral profile $h_n(\theta)$ Amplitude of the longitudinal shift between two adjacent spiral segments as a function of the azimuthal angle coordinate α Parameter related to step transition function width P(θ) Percentage of the spiral track occupied by the step transition function as a function of the azimuthal angle coordinate

The invention claimed is:

1. An intraocular lens comprising:

a transparent body with an anterior surface and a posterior surface having an optical axis intersecting centers of the anterior and the posterior surfaces;

a base refractive power ($\Phi_{IOL}$) range defined by base topologies of the anterior and posterior surfaces combined, as defined by an equation $$\Phi_{IOL} = \frac{(n_{IOL} - n_{aq})}{R_{ant}} + \frac{(n_{vit} - n_{IOL})}{R_{pos}} - \left[\frac{(n_{IOL} - n_{aq})}{R_{ant}} \cdot \frac{(n_{vit} - n_{IOL})}{R_{pos}} \cdot \frac{t_{IOL}}{n_{IOL}}\right];$$

wherein $n_{IOL}$ is a refraction index of the intraocular lens, $n_{ag}$ is a refraction index of an aqueous humor, $n_{vit}$ is a refraction index of a vitreous humor, $R_{ant}$ is a radius of curvature of the anterior surface, $R_{pos}$ is a radius of curvature of the posterior surface and $t_{IOL}$ is a central thickness of the intraocular lens; and spiral tracks on at least one surface of said anterior and posterior surfaces to provide an additional power distribution along said spiral tracks, wherein said spiral tracks originate from a center or an outer edge of a central zone of said surface, extend towards a periphery of the lens, and end at said periphery or at some point within said surface, wherein said surface has a spiral grid formed by said surface in a zone of one of said spiral tracks being shifted axially with respect to said surface in a zone of an adjacent one of said spiral tracks in a step-like helicoidal pattern following internal and external edges of the spiral tracks, the zones thereby forming shifted zones, wherein in said step-like helicoidal pattern a transition region is introduced between the shifted zones, and wherein said transition region occupies part of at least one of the spiral tracks to which it transitions in a radial direction, or occupies a full width of said spiral track.

2. The intraocular lens of claim 1, wherein the transition function ($z_{step}$) introduced between shifted zones is described by a Taylor series, a Fourier series, Bessel functions, Jacobi polynomials or Lagrange polynomials or by an equation $$z_{step} = h_n(\theta)\frac{\left[\sin\left(\alpha\pi + \frac{\pi}{2}\right) + 1\right]}{2},$$

wherein $h_n(\theta)$ is the amplitude of the step in the transition of track n to n+1, and $$\alpha = \frac{r - r_{int}}{100 \cdot P(\theta) \cdot (r_{ext} - r_{int})},$$

which depend on the azimuthal angle (θ) and the radial position (r) where $r_{int}$ and $r_{ext}$ are the internal and external limits of the spiral track in the radial position and P(θ) is the percentage of the track width used in the transition, which can vary from 0% to 100% of the spiral track width, with r limited to the transition region.

3. The intraocular lens according to claim 2, wherein said amplitude of said stop is constant or varies along the spiral track.

4. The intraocular lens according to claim 3, wherein said amplitude of said step is equal to an amplitude of another step defined on the same surface; or said amplitude of said step is different to said amplitude of another step defined on the same surface.

5. The intraocular lens according to claim 4, wherein a radial position (r) of said spiral track is described by equation $$r = a * \theta^{\beta} + b,$$

which depends on the azimuthal angle (θ) and wherein a is a parameter related to a thickness of the spiral track and b is a parameter related to a radial starting point of the spiral track, a parameter β can vary from −2 to 2, specifically when β is equal to 1, the previous equation leads to an Archimedean spiral, when β is equal to ½, it leads to a Fermat spiral, when β is equal to −½ it leads to a Lituus spiral, when β is equal to −1 it leads to a Hyperbolic spiral; or wherein the radial position (r) of the spiral track is described by a Logarithmic spiral that follows equation $$r = a * e^{\beta * \theta} + b,$$

which depends on the azimuthal angle (θ) and the parameter β, which varies from −2 to 2, and wherein a is a parameter related to a thickness of a given spiral track and b is a parameter related to a radial starting point of the spiral track.

6. The intraocular lens according to claim 5, wherein the spiral grid has a number of spiral tracks in a range of 1 to 200, and are contiguous, sparse or juxtaposed.

7. The intraocular lens according to claim 6, wherein the spiral grid has a number of turns in a range of 1 to 200 include complete or incomplete turns.

8. The intraocular lens according to claim 1, wherein a power variation along the spiral track is deployed on the anterior, posterior or both surfaces.

9. The intraocular lens according to claim 8, wherein the anterior and/or posterior surfaces are convex, concave or flat.

10. The intraocular lens according to claim 8, wherein the base topologies of the anterior surface, posterior surface or both surfaces, are simple aspheric, spherical, toric, or have a base refractive power range changed by a multi-aspheric function (Z(r)) described by equation $$Z(r) = \frac{c \cdot r^2}{1 + \sqrt{1 - (1 + k(r))c^2 r^2}},$$

which depends on a radial position (r) and a conic transition function (k(r)) and wherein c is a curvature associated with a radius of curvature of a given surface of the lens;

said multi-aspheric function formulated dividing the lens radius in N radial segments, with N being an integer in a range of 1 to 10,000 (ten thousand), and $K_1$ to $K_{N+1}$ defining a conic value at a beginning and an end of each segment which can assume any real number in a range of from −1,000 (minus one thousand) to 1,000 (one thousand), and a transition function connecting two adjacent segments.

11. The intraocular lens according to claim 10, wherein the base topologies of the anterior surface, posterior surface or both surfaces have a base refractive power range changed by the multi-aspheric function (Z(r)) and wherein the transition function connecting two adjacent segments of a multi-aspheric base ($k_n(r)$) is defined by a Taylor series, a Fourier series, Bessel functions, Jacobi polynomials or Lagrange polynomials;

or the transition function connecting two adjacent segments of the multi-aspheric base ($k_n(r)$) is defined by $$k_n(r) = \left[\frac{(K_{n+1} - K_n)}{\Delta}\right][r - (n-1)\Delta] + K_n,$$

where the radial position (r) varies from Δ·(n−1) to Δ·n and wherein Δ is a parameter that controls a radial width of a given aspheric segment;

or the transition function connecting two adjacent segments of the multi-aspheric base ($k_n(r)$) is defined by $$k_n(r) = \beta_n K_n + (1 - \beta_n) K_{n+1},$$

where $$\beta_n = \frac{\left\{1 + \sin\left[\frac{\pi(r - (n-1)\Delta)}{\Delta} + \frac{\pi}{\Delta}\right]\right\}}{2}$$

and the radial position (r) varies from Δ·(n−1) to Δ·n and wherein Δ is a parameter that controls a radial width of a given aspheric segment.

12. The intraocular lens according to claim 11, wherein the lens comprises multifocal or extended-depth-of-focus characteristics that are maintained or morphed across different pupil sizes.

13. A method of manufacturing the intraocular lens according to claim 1 comprising using diamond turning, casting, hot stamping, injection molding or lithographic pattern wet and dry etching, and variations or combinations thereof;

wherein said method relies on RIS (Refractive-Index Shaping) by a femtosecond laser, or a Laser Induced Refractive Index Change (LIRIC) to generate refractive power variations along spiral tracks; and wherein said lens is manufactured using materials that are rigid or foldable, hydrophobic or hydrophilic, methacrylate-based or silicone, such as PMMA, collamers, macromers, hydrogels, and acrylates.

* * * * *